(12) United States Patent
Murphy et al.

(10) Patent No.: US 10,022,052 B2
(45) Date of Patent: Jul. 17, 2018

(54) METHOD OF CHARACTERIZING WOUNDS WITH RAMAN SPECTROSCOPY

(71) Applicants: Christopher J. Murphy, Madison, WI (US); Nicholas L. Abbott, Madison, WI (US); Jonathan McAnulty, Oregon, WI (US); Rishabh Jain, Madison, WI (US)

(72) Inventors: Christopher J. Murphy, Madison, WI (US); Nicholas L. Abbott, Madison, WI (US); Jonathan McAnulty, Oregon, WI (US); Rishabh Jain, Madison, WI (US)

(*) Notice: Subject to any disclaimer, the term of this patent is extended or adjusted under 35 U.S.C. 154(b) by 0 days.

(21) Appl. No.: 14/908,928

(22) PCT Filed: Jul. 25, 2014

(86) PCT No.: PCT/US2014/048104
§ 371 (c)(1),
(2) Date: Jan. 29, 2016

(87) PCT Pub. No.: WO2015/017258
PCT Pub. Date: Feb. 5, 2015

(65) Prior Publication Data
US 2016/0198994 A1    Jul. 14, 2016

Related U.S. Application Data

(60) Provisional application No. 61/861,245, filed on Aug. 1, 2013.

(51) Int. Cl.
    A61B 5/00   (2006.01)
    A61B 90/30  (2016.01)
(52) U.S. Cl.
    CPC .......... *A61B 5/0075* (2013.01); *A61B 5/445* (2013.01); *A61B 5/486* (2013.01); *A61B 5/7282* (2013.01); *A61B 2090/306* (2016.02); *A61B 2560/0425* (2013.01); *A61B 2576/00* (2013.01)
(58) Field of Classification Search
    CPC ..... A61B 5/0071; A61B 5/486; A61B 5/1455; A61B 5/0059; A61B 5/0075; A61B 5/0082; A61B 5/6898; A61B 5/7235; A61B 5/7264; A61B 5/7271; G01J 3/0264; G01J 3/0272
    See application file for complete search history.

(56) References Cited

U.S. PATENT DOCUMENTS 8,064,976 B2 * 11/2011 Ince ............... A61B 5/0261 600/343
2006/0074282 A1 * 4/2006 Ward ............... A61B 5/0071 600/310

* cited by examiner

*Primary Examiner* — Deborah Malamud
(74) *Attorney, Agent, or Firm* — Casimir Jones, S.C.

(57) ABSTRACT

The present invention relates to methods and devices for characterizing wounds, and in particular to the use of Raman spectroscopy to characterize the state of healing of a wound.

14 Claims, 16 Drawing Sheets

मेथड OF CHARACTERIZING WOUNDS WITH RAMAN SPECTROSCOPY

METHOD OF CHARACTERIZING WOUNDS WITH RAMAN SPECTROSCOPY

FIELD OF THE INVENTION

The present invention relates to methods and devices for characterizing wounds, and in particular to the use of Raman spectroscopy to characterize the state of healing of a wound.

BACKGROUND OF THE INVENTION

Nearly 6.5 million people in the United States suffer from chronic wounds and annual treatment costs exceeds $25 billion (1). A wide variety of treatment options exist (2) but clinicians often try multiple treatments until find one that promotes further the healing process for a particular patient. The healing of wounds is conceptually thought to occur in distinct, overlapping stages—it begins with hemostasis, followed by a stage in which inflammation is prevalent, which in turn leads to a stage where formation of granulation tissue, cell proliferation, angiogenesis and re-epithelialization are dominant (3). Non-healing or slowly healing (chronic) wounds are typically characterized as being stuck in a persistent, inflammatory stage, unable to make a transition to the cell-proliferative stage. The evaluation of non-healing wounds is difficult, however, and is usually performed qualitatively based on gross visual examination (4, 5) that requires high skill and experience (6). It may also sometimes require biopsies at multiple locations of a wound followed by lengthy histological analyses (7, 8). A simple and fast method that characterizes healing progress in a wound has the potential to expedite clinical diagnosis, better inform treatment, ultimately reducing discomfort and promoting favorable wound healing outcomes for patients.

Several non-invasive, optical methods have shown promise for characterizing physical characteristics of wounds in vivo such as cutaneous blood flow and microcirculation (laser Doppler perfusion imaging), tissue structure (optical coherence tomography) and tissue temperature (thermal imaging) (9). However, biochemical characteristics of healing wounds can reliably be evaluated only by tissue biopsy followed by histology (10). In addition to being invasive, this method is tedious, laborious (11) and prone to subjective evaluation (12, 13). Raman spectroscopy holds the potential to simply and rapidly assess the biochemistry of a wound in situ and thus complement traditional histological approaches. Raman spectroscopy relies on the inelastic (Raman) scattering of photons incident on a material which absorb or release energy from vibrational modes of chemical bonds giving rise to frequency (i.e., energy) shifts in the photons (14). These 'Raman' shift frequencies are unique to individual chemical bonds and can help identify the chemical composition of a material. Various biological tissues have been analyzed by Raman spectroscopy and it has also been shown to be able to identify diseased tissue in ailments such as breast cancer, atherosclerosis and Alzheimer's disease (15). Past studies (16-18) have also measured Raman spectra of wounds but no study has demonstrated the use of the method to distinguish between different stages of wound healing in vivo. In particular, past analyses of the Raman spectra of wounds has been based on differences in individual Raman peaks or peak ratios that were assigned to specific proteins. This approach is of limited diagnostic utility with complex biological tissue because many different tissue components are made from common molecular structural units (amino-acids, sugars, fatty acids) and bonds.

Bacterial contamination and colonization occurs in almost all wounds and non-virulent strains of bacteria, in low numbers, have been shown to facilitate healing (19-20). However, underlying co-morbidities (diabetes, venous stasis, etc.), and host factors (poor blood perfusion, white blood cell dysfunction, hyperglycemia, etc.) can promote bacterial overgrowth (21) that delays healing. For example, infection by *Staphylococcus aureus*, *Pseudomonas aeruginosa* and β-hemolytic *Streptococci* has been implicated in delayed healing (21) via production of destructive enzymes and toxins (20). Elevated endotoxin production provokes increased production of pro-inflammatory cytokines such as IL-1 and tumor necrosis factor-α (22-23) which in turn increase matrix metalloproteases that degrade endogenous growth factors. Thus, the excessive inflammatory response provoked by bacteria is hypothesized to underlie formation of chronic wounds. In addition, the moist environment of a wound provides an ideal milieu for bacteria to form complex communities in a self-secreted extracellular polysaccharide matrix (EPS) known as a biofilm (20-21, 24-25). Over time, biofilms mature with complex microstructures such as water channels for transfer of nutrients, waste and intercellular signaling molecules ('quorum sensing' molecules) (26) creating protected microenvironments for microbial persistence.

Biofilm bacteria communicate via quorum-sensing and respond collectively to the environment, enhancing resistance to antimicrobial agents (including antibiotics, antiseptics) and host defense mechanisms (24). Their EPS layer provides a diffusion barrier to topical antibiotics and contains substances like alginate which scavenges free oxygen radicals, prevents phagocytosis, and binds cationic antibiotics such as aminoglycosides (27). Biofilm bacteria can also slow their metabolism to increase their survival rates (20). Furthermore, genotypic and phenotypic diversity within a biofilm makes it likely that some cells survive when challenged by external stresses (28). While characterizing biofilms in vitro is facile due to availability of various staining methods (29, 30), characterization in vivo is highly challenging because the complex background of host tissue makes visual assessment (by light or electron microscopy) difficult and because host tissues adsorb biofilm stains non-specifically. More elaborate methods (viz. in vitro culture of wound swabs (31, 32)) can be inaccurate and do not readily distinguish between biofilms versus planktonic microbes. Development of rapid and non-invasive methods for in situ identification of biofilms (e.g. using a Raman microspectroscopic approach) would allow clinicians to alter treatment strategies for biofilm eradication in real time, including physical debridement, antimicrobial wound dressings and use of various topical antimicrobials and antibiofilm agents (28). Furthermore, diagnosis of biofilm formation prior to maturation has the potential to substantially decrease the likelihood of dysregulation of the wound healing process and thus formation of chronic wounds.

SUMMARY OF THE INVENTION

The present invention relates to methods and devices for characterizing wounds, and in particular to the use of Raman spectroscopy to characterize the state of healing of a wound.

In some embodiments, the present invention provides methods of characterizing a wound comprising: collecting one or more or a plurality of Raman spectra from a wound in a patient, via a processor, comparing the plurality of Raman spectra with one or more basis spectra to determine one or more factor loadings, and correlating the factor loadings to the healing stage of the wound. In some embodiments, collecting comprises analyzing the wound with a handheld Raman microspectroscope. In some embodiments, collecting comprises analyzing a wound in a live subject with a fiber optic probe operably linked to a Raman microspectroscope. In some embodiments, the wound is illuminated with laser emitted from the fiber optic probe at a desired wavelength. In some embodiments, the healing stage is selected from the group consisting of hemostasis, the inflammation stage and the proliferative stage.

In some embodiments, the methods further comprise the step of determining a course of treatment based on the healing stage identified by comparison of the one or more Raman spectra with one or more basis spectra. In some embodiments, the methods further comprise identifying healing and non-healing portions in the same wound on basis of their Raman spectra to inform a course of treatment selective to the non-healing portions. In some embodiments, the methods further comprise the step of using the Raman spectra to identify the presence of microorganisms. In some embodiments, the microorganisms are associated in a biofilm.

In some embodiments, the plurality of Raman spectra are decomposed by multivariate factor analysis to provide one or more factor loading values corresponding to the healing stage of a wound. In some embodiments, the plurality of Raman spectra are decomposed by multivariate factor analysis to provide three factor loading values each corresponding to a respective wound healing stage. In some embodiments, the wound healing stage is selected from the group consisting of the hemostasis stage, the inflammation stage and the proliferative stage.

In some embodiments, the present invention provides methods of identifying basis spectra and factor loadings for use in characterizing the healing stage of a wound comprising: via a computer processor, decomposing measured Raman spectra from a plurality of wounds at different stages of healing into basis spectra by multivariate factor analysis; and assigning factor loadingsby determining weights for each basis spectrum as a function of time for different stages of wound healing. In some embodiments, the wound healing stage is selected from the group consisting of the hemostasis stage, the inflammation stage and the proliferative stage. In some embodiments, the measured Raman spectrum is decomposed into at least three basis spectra.

In some embodiments, the present invention provides a system for analysis of wound healing comprising a Raman microspectroscope in operable association with a computer processor, the computer processor comprising a nontransitory computer readable medium comprising a database of basis spectra derived from Raman spectroscopic analysis of a plurality of wound beds and computer executable code that compares Raman spectra collected from a subject via the Raman microspectroscope with the basis spectra to determine a stage of wound healing. In some embodiments, the Raman microspectroscope is handheld. In some embodiments, the basis spectra correspond to stages of wound healing.

In some embodiments, the present invention provides methodd comprising analyzing a measured Raman spectrum from a subject with the system described above by comparing the measured Raman spectrum with one or more basis spectra to characterize the healing stage of the wound.

In some embodiments, the present invention provides methods of diagnosing surface ocular disorders comprising: collecting a plurality of Raman spectra from a subject ocular surface, and via a processor, comparing the Raman spectra with one or more basis spectra to determine one or more factor loadings which are correlated to one or more parameters of the ocular surface.

In some embodiments, the present invention provides a nontransitory computer readable medium comprising a database of basis spectra derived from Raman spectroscopic analysis of one or more wound beds and computer executable code that compares Raman spectra collected from a subject via the Raman microspectroscope with the basis spectra to determine a stage of wound healing.

In some embodiments, the present invention provides methods of characterizing an engineered tissue comprising: collecting a plurality of Raman spectra from an engineered tissue, and via a processor, comparing the Raman spectra with one or more basis spectra to determine one or more factor loadings which are correlated to a parameter of the engineered tissue.

DESCRIPTION OF THE FIGURES

FIG. 2: (A) Factor score spectra (normalized and scaled) from MFA (B) Average factor loadings from MFA (normalized and scaled). Error bars indicate±SEM.

DETAILED DESCRIPTION OF THE INVENTION

Figure 1:
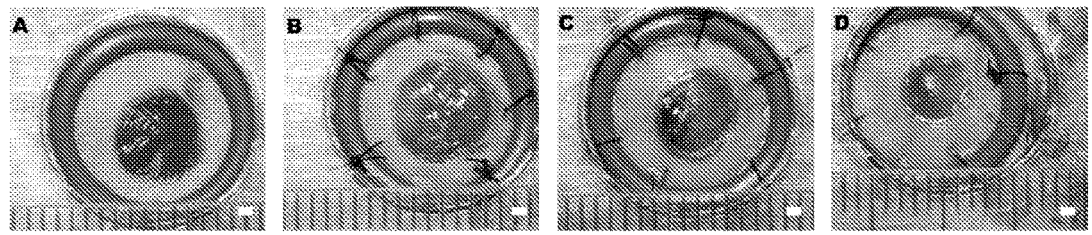
FIG. 1: 'Splinted' wounds in mice on (A) day 0 (B) day 1 (C) day 5 and (D) day 7.

The present invention relates to methods and devices for characterizing wounds, and in particular to the use of Raman spectroscopy to characterize the state of healing of a wound. It is contemplated that accurate and rapid diagnosis of the stage of healing of a wound in a simple and non-invasive manner enables clinicians to promptly alter non-functional treatments and hasten the resolution of non-healing wounds. Histochemical characterization of biopsied wound tissue, however, is currently the only reliable method despite being invasive, complex and laborious. The present invention encompasses the use of Raman microspectroscopy coupled with multivariate spectral analysis as a simple, non-invasive method to biochemically characterize healing wounds and accurately identify different phases of healing at different time-points. Raman spectra were collected from 'splinted' wounds in mice at 4 different time-points (0, 1, 5 and 7 days) corresponding to different phases of wound healing (verified using histopathologic analysis). Spectra were deconvolved using multivariate factor analysis (MFA) into 3 'factor score spectra' which in turn were successfully correlated with spectra of prominent wound bed constituents (namely, collagen, lipids, fibrin, fibronectin, etc.) using non-negative least squares (NNLS) fitting. The factor loadings (weights) for spectra that belonged to wounds at different time-points provided a quantitative measure of wound healing progress in terms of key parameters such as inflammation and granulation. Wounds in similar healing stages were characterized by clusters of loading values and slowly healing wounds amongst them were successfully identified as 'outliers'.

The present invention provides a useful non-invasive technique that provides insight into the status of healing wounds and can be used as a complementary tool for real-time, in situ biochemical characterization in wound healing studies and clinical diagnosis. The data herein demonstrate that spectra for different components differ significantly when peak locations and intensities are considered in aggregate. In preferred embodiments, multivariate statistics enables the evaluation of aggregated differences in spectra across a wide wavenumber range. In this context, it is noted that the spatial distribution of collagen and elastin during re-epithelialization in an explant skin culture wound model has been reported using Raman imaging coupled with multivariate statistical analysis (18). However, this previous study could not characterize changes associated with homeostasis or inflammation in wounds (because they used an explant skin culture model). In contrast, the present invention employs Raman spectroscopy in a well-characterized animal wound model—the excisional 'splinted' wound in mouse that closely mimics the healing of full-thickness wounds in humans (33). A methodology is provided that distinguishes between different stages of wound healing on the basis of an aggregate of biochemical markers (associated with the different stages) that are identified by Raman spectroscopy. In preferred embodiments, Raman spectra that are collected from a wound are subjected to multivariate factor analysis (MFA) to yield analogous factor 'loadings' which serve as objective, quantitative measures in the assessment of healing of the wounds.

In some embodiments, the present invention provides methods of identifying basis spectra for use in characterizing the healing stage of a wound comprising, via a computer processor, decomposing measured Raman spectra from a plurality of wounds as a function of healing into signature basis spectra by multivariate factor analysis. Similarly, the present invention provides methods for use in characterizing the microbial burden and presence of biofilms of wounds by decomposing microbially burdened wounds and biofilm-covered wounds, via a computer processor, decomposing measured Raman spectra from a plurality of wounds as a function of microbial burden into signature basis spectra by multivariate factor analysis. These basis spectra will be stored on a computer and can be used for future determination of the stage of healing or status of microbial burden of a wound.

In some embodiments, the present invention provides methods of identifying basis spectra for use in characterizing the healing stage of a wound comprising, via a computer processor, decomposing a measured Raman spectrum from a wound into basis spectra by multivariate factor analysis; and determining weighting for each basis spectrum as a function of time to describe a stage of wound healing. In some embodiments, the measured Raman spectrum is decomposed into at least three basis spectra. In some embodiments, the basis spectra each correlate to a stage of wound healing. In some embodiments, the wound healing stage is selected from the group consisting of the hemostasis stage, inflammation stage and the proliferative stage. In some embodiments, the one or more Raman spectra are decomposed by multivariate factor analysis to provide one or more factor loading values corresponding to the healing stage of a wound. In some embodiments, the one or more Raman spectra are decomposed by multivariate factor analysis to provide three factor loading values each corresponding to a respective wound healing stage.

Another embodiment of the invention permits assessment of the growth of engineered tissue or constructs being fabricated to replace mammalian tissue. In this context, Raman spectra of engineered tissue, or a tissue being prepared for regenerative medicine, is compared to signature basis spectra that are obtained by measurement of native tissue (e.g., a liver) or previously engineered tissue. The engineered tissue can be in vivo or in vitro.

In further embodiments, the present invention provides methods of characterizing a wound comprising making one or more Raman spectra of a wound in a patient, and via a processor, comparing the one or more Raman spectra with one or more signature basis spectra to determine one or more factor loadings which are correlated to the healing stage of the wound. In some embodiments, the wound is analyzed with a handheld Raman microspectroscope. In some embodiments, the healing stage is selected from the group consisting of the hemostasis stage, the inflammation stage and the proliferative stage. In some embodiments, a course of treatment is determined based on the healing stage identified by comparison of the one or more Raman spectra with one or more basis spectra. In some embodiments, the Raman spectra is further utilized to identify the presence of microorganisms. In some embodiments, the microorganisms are associated in a biofilm.

The present invention provides methods and materials to assist medical or research professionals in determining the healing stage of a wound. Medical professionals can be, for example, doctors, nurses, medical laboratory technologists, and pharmacists. Research professionals can be, for example, principle investigators, research technicians, post-doctoral trainees, and graduate students. A professional can be assisted by (1) determining the healing stage of a wound in a subject and (2) communicating information about the healing stage to that or another professional, for example.

After the stage of wound healing (e.g., stage or score) is reported, a medical professional can take one or more actions that can affect patient care. For example, a medical professional can record the results in a patient's medical record. In some cases, a medical professional can record a diagnosis or determination of the stage of wound healing or associated disease, or otherwise transform the patient's medical record, to reflect the patient's medical condition. In some cases, a medical professional can review and evaluate a patient's entire medical record, and assess multiple treatment strategies, for clinical intervention of a patient's condition. In some cases, a medical professional can record a prediction of disease progression. In some cases, a medical professional can review and evaluate a patient's entire medical record and assess multiple treatment strategies, for clinical intervention of a patient's condition.

A medical professional can initiate or modify treatment of the wound or associated disease after receiving information regarding the stage of wound healing. In some cases, a medical professional can compare previous reports and the recently communicated information on the stage of wound healing, and recommend a change in therapy. In some cases, a medical professional can enroll a patient in a clinical trial for novel therapeutic intervention. In some cases, a medical professional can elect waiting to begin therapy until the patient's symptoms require clinical intervention.

A medical professional can communicate the assay results to a patient or a patient's family. In some cases, a medical professional can provide a patient and/or a patient's family with information regarding healing of the wound or associated diseases, including treatment options, prognosis, and referrals to specialists, e.g., immunologists or gastroenterologists. In some cases, a medical professional can provide a copy of a patient's medical records to communicate assay results to a specialist. A research professional can apply information regarding a subject's assay results to advance disease research. For example, a researcher can compile data on the assay results, with information regarding the efficacy of a specific treatment of a wound to identify an effective treatment. In some cases, a research professional can obtain assay results to evaluate a subject's enrollment, or continued participation in a research study or clinical trial. In some cases, a research professional can classify the severity of a subject's condition, based on assay results. In some cases, a research professional can communicate a subject's assay results to a medical professional. In some cases, a research professional can refer a subject to a medical professional for clinical assessment of disease, and treatment thereof. Any appropriate method can be used to communicate information to another person (e.g., a professional). For example, information can be given directly or indirectly to a professional. For example, a laboratory technician can input the assay results into a computer-based record. In some cases, information is communicated by making a physical alteration to medical or research records. For example, a medical professional can make a permanent notation or flag a medical record for communicating a diagnosis to other medical professionals reviewing the record. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

In some embodiments, the methods disclosed herein are useful in monitoring the treatment of a wound or disease associated with the wound. For example, in some embodiments, the methods may be performed immediately before, during and/or after a treatment to monitor treatment success. In some embodiments, the methods are performed at intervals during wound treatment to ensure treatment success.

The present invention also provides a variety of computer-related embodiments. Specifically, in some embodiments, the invention provides a nontransitory computer readable medium comprising a database of basis spectra derived from Raman spectroscopic analysis of one or more wound beds and computer executable code that compares Raman spectra collected from a subject via the Raman microspectroscope with the basis spectra to determine a stage of wound healing. In some embodiments, the computer facilitates collection and entry into a computer raman spectra obtained by scanning a patient with a system of the present invention. In some embodiments, the computer executable code allows comparison and analysis of spectra taken at least at two different time points. In some embodiments, the first pattern of spectra may be indicative of wound in a particular stage of healing such as the hemostasis stage and the second pattern of spectra may be indicative of a more advanced stage in the wound healing process such as the inflammation stage and the proliferative stage. In such embodiments, the comparing provides for monitoring of the progression of wound healing from the first time point to the second time point. If wound healing is not advancing through the normal stages, a change in therapy or altered therapy may be suggested.

In some embodiments, the present invention provides a system for analysis of wound healing comprising a computer processor and a nontransitory computer readable medium comprising basis spectra derived from Raman spectroscopy analysis of a wound bed. In some embodiments, the systems further comprise a Raman microspectroscope. In some embodiments, the Raman microspectroscope is handheld. In some embodiments, the Raman microspectroscope is in operable association with a handheld fiber optic probe that can be used to illuminate a wound in a living subject. The fiber optic probe preferably emits a light (e.g., via a laser as an excitation source) having a desired wavelength. In some embodiments, the desired wavelength is from about 400 nm to about 900 nm, more preferably from about 480 nm to 580 nm, from 735 nm to 835 nm, or from about 700 nm to 900 nm, and most preferably about 785 nm. In some embodiments, the basis spectra correspond to stages of wound healing. In some embodiments, the systems are used to analyze a measured Raman spectrum obtained from a wound in a patient by comparing the measured Raman spectrum with one or more basis spectra to characterize the healing stage of the wound. In some embodiments, the response of a wound to a course of treatment is determined by comparison of the one or more Raman spectra of the wound with one or more signature basis spectra.

The methods and systems described herein can be implemented in numerous ways. In one embodiment, the methods involve use of a communications infrastructure, for example the internet. Several embodiments of the invention are discussed below. It is also to be understood that the present invention may be implemented in various forms of hardware, software, firmware, processors, distributed servers (e.g., as used in cloud computing) or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site (e.g., at a service provider's facility).

For example, during or after data input by the user, portions of the data processing can be performed in the user-side computing environment. For example, the user-side computing environment can be programmed to provide for defined test codes to denote platform, carrier/diagnostic test, or both; processing of data using defined flags, and/or generation of flag configurations, where the responses are transmitted as processed or partially processed responses to the reviewer's computing environment in the form of test code and flag configurations for subsequent execution of one or more algorithms to provide a results and/or generate a report in the reviewer's computing environment.

The application program for executing the processes described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which generally includes test data (e.g., specific gene products assayed), and test result data (e.g., the pattern of hematological neoplasm-specific marker detection results from a sample). This information received can be stored at least temporarily in a database, and data analyzed in comparison to a library of basis spectra.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In some embodiments, all or a portion of the input data and/or all or a portion of the output data (e.g., usually at least the library of the pattern of hematological neoplasm-specific marker detection results known to be indicative of the presence or absence of a pre-cancerous condition) are maintained on a server for access, e.g., confidential access. The results may be accessed or sent to professionals as desired.

A system for use in the methods described herein generally includes at least one computer processor (e.g., where the method is carried out in its entirety at a single site) or at least two networked computer processors (e.g., where spectra for a subject is to be input by a user (e.g., a technician or someone performing the assays)) and transmitted to a remote site to a second computer processor for analysis, where the first and second computer processors are connected by a network, e.g., via an intranet or internet). The system can also include a user component(s) for input; and a reviewer component(s) for review of data, and generation of reports, including diagnosis or characterization of a disease. Additional components of the system can include a server component(s); and a database(s) for storing data (e.g., as in a database of report elements), or a relational database (RDB) which can include data input by the user and data output. The computer processors can be processors that are typically found in personal desktop computers (e.g., IBM, Dell, Macintosh), portable computers, mainframes, minicomputers, tablet computer, smart phone, or other computing devices.

The input components can be complete, stand-alone personal computers offering a full range of power and features to run applications. The user component usually operates under any desired operating system and includes a communication element (e.g., a modem or other hardware for connecting to a network using a cellular phone network, Wi-Fi, Bluetooth, Ethernet, etc.), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe, or distributed across multiple servers (e.g., as in cloud computing applications) and offers data management, information sharing between clients, network administration and security. The application and any databases used can be on the same or different servers. Other computing arrangements for the user and server(s), including processing on a single machine such as a mainframe, a collection of machines, or other suitable configuration are contemplated. In general, the user and server machines work together to accomplish the processing of the present invention.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

EXAMPLES

Creation of Wounds in Mice and Harvesting of Wounds

All experimental protocols were approved by the Institutional Animal Care and Use Committee of the University of Wisconsin. BalbC mice (Jackson Laboratories, Inc.) between the ages of 8 to 16 weeks were used for the studies. Mice were housed in groups during a 1-week acclimation period before the study and housed individually after procedure. Throughout the study period, mice were maintained in a temperature-controlled facility with a standard light/dark cycle. All mice were provided with environmental enrichment and food and water ad libitum. Mice were randomly assigned to experimental groups on the day of surgery, and body weights were recorded after surgery and on days 1 and 3 and on the day prior to euthanasia.

Mice were anesthetized with 2% inhaled isoflurane, administered using an induction chamber. The mice were injected with buprenorphine (0.001 mg) for analgesia prior to wounding. Mice were shaved on cranial dorsal region and back nails trimmed. Shaved area was aseptically prepped with Betasept Scrub (4% chlorhexidine gluconate) and sterile saline (0.9%) 3 times each using sterile CTAs (cotton tipped applicators). Silicone splints (11 mm×1.75 mm O-ring, O-Ring Warehouse #0568-013) were glued to skin, one on each side of midline with CrazyGlue Gel. Six simple interrupted sutures were placed with either 5-0 Monosef (Covidien) or 5-0 Ethilon (Ethicon) suture equidistant around O-ring. Two 6 mm wounds were created using a 6 mm biopsy punch (Milltex, Inc). For mice wounds not being harvested at initial timepoint, a 14 mm plastic coverslip was glued to splint with CrazyGlue Gel and then covered with tegaderm. Mice were recovered from anesthesia on a warming pad until ambulatory and then returned to colony. Upon completion of each timepoint mice were euthanized with an intraperitoneal injection of Beuthanasia-D (Schering-Plough) solution (0.5 mL per mouse) after induction of anesthesia as described above.

Wounds were harvested for collection of Raman spectra and histopathalogical analysis using iris scissors and eye dressing forceps. A square of tissue was cut around outside of O-ring and placed in a tissue cassette for later placement in 10% formalin.

Experiments were repeated on four separate batches of mice (designated as WT1 to WT4 in manuscript) at different times following the same protocol as above. Histopathologic analysis was performed on all mice wounds belonging to batches WT3 and WT4. In batch WT2, Histopathologic analysis was performed on half of the wounds and Raman spectra was collected from the other half of the wounds. Table 1 indicates the no. of mice in different batches assigned for harvesting of wounds at different time-points.

TABLE 1

No. of mice in different batches according to time-point of harvesting of wounds

| Batch | No. of mice | | | |
|---|---|---|---|---|
| | Day 0 | Day 1 | Day 5 | Day 7 |
| WT1 | 4 | 4 | 4 | — |
| WT2 | 4 | 5 | 5 | — |
| WT3 | 6 | 7 | — | 7 |
| WT4 | 3 | 5 | 5 | 5 |

Raman Spectral Analysis

Figure 9:
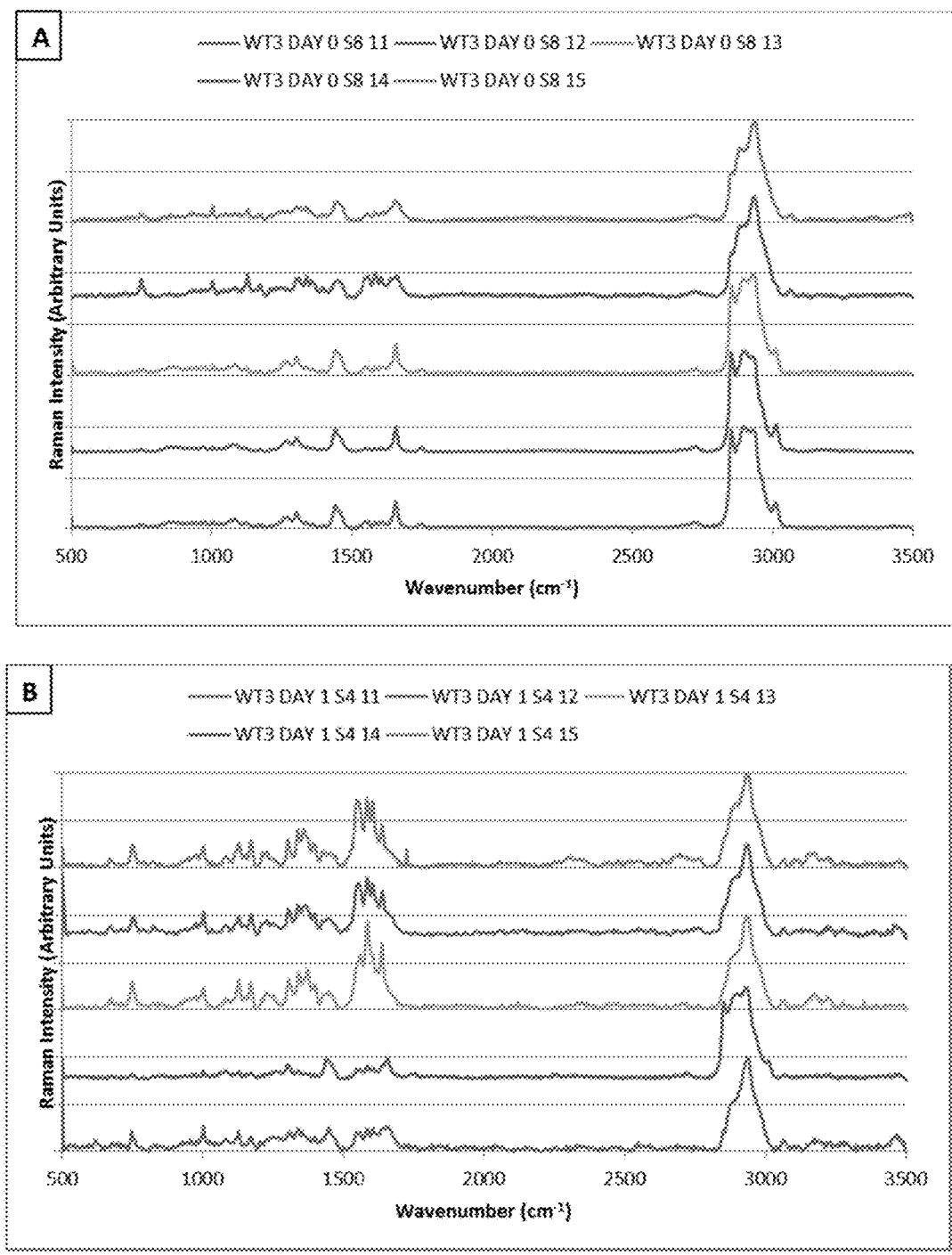
FIG. 9: Raman Spectra collected from different random regions on the same wound are different and reflect spatial heterogeneity in a wound. Spectra collected from 5 different points of a wound harvested on (A) Day 0 (B) Day 1 (C) Day 5 and (D) Day 7. In our study, spectra collected from different points were averaged to represent the entire wound.
Figure 9:
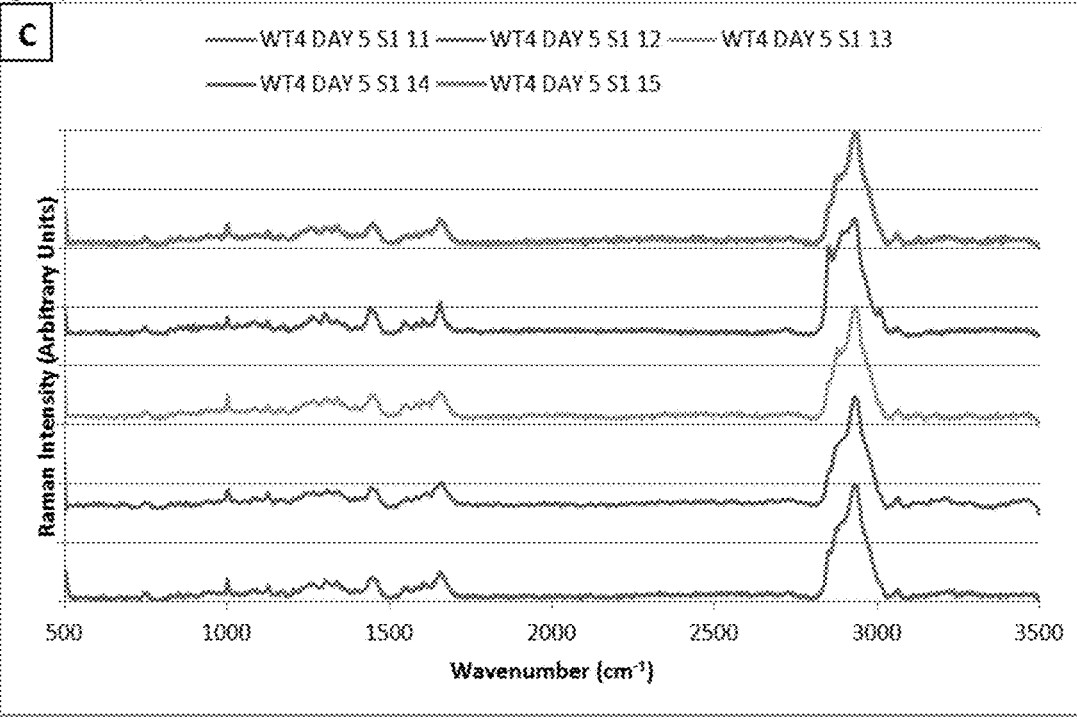
Figure 9:
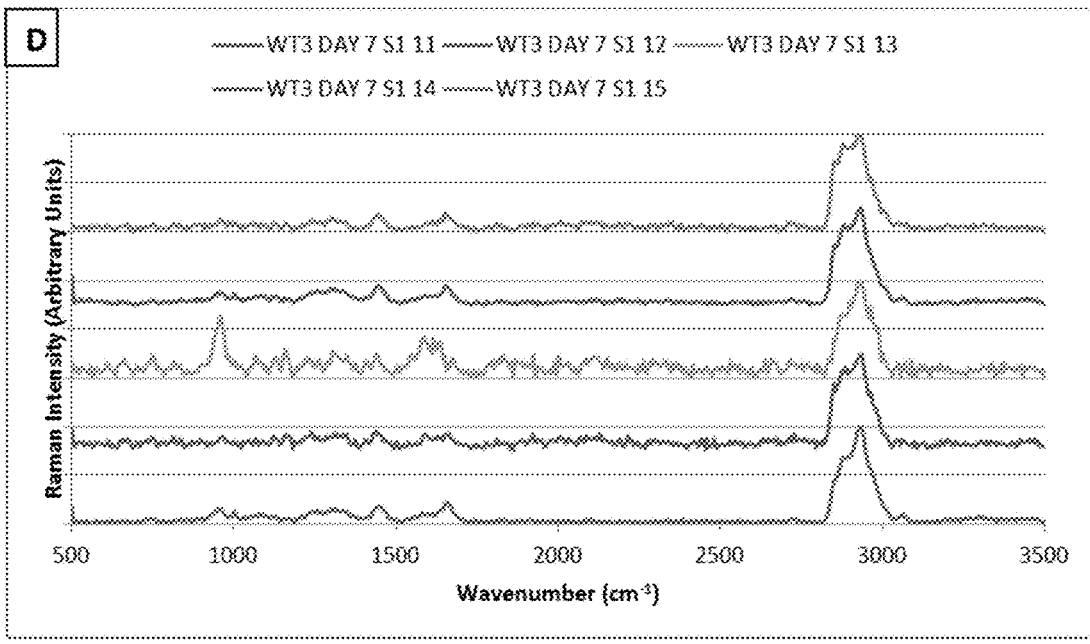
Figure 10:
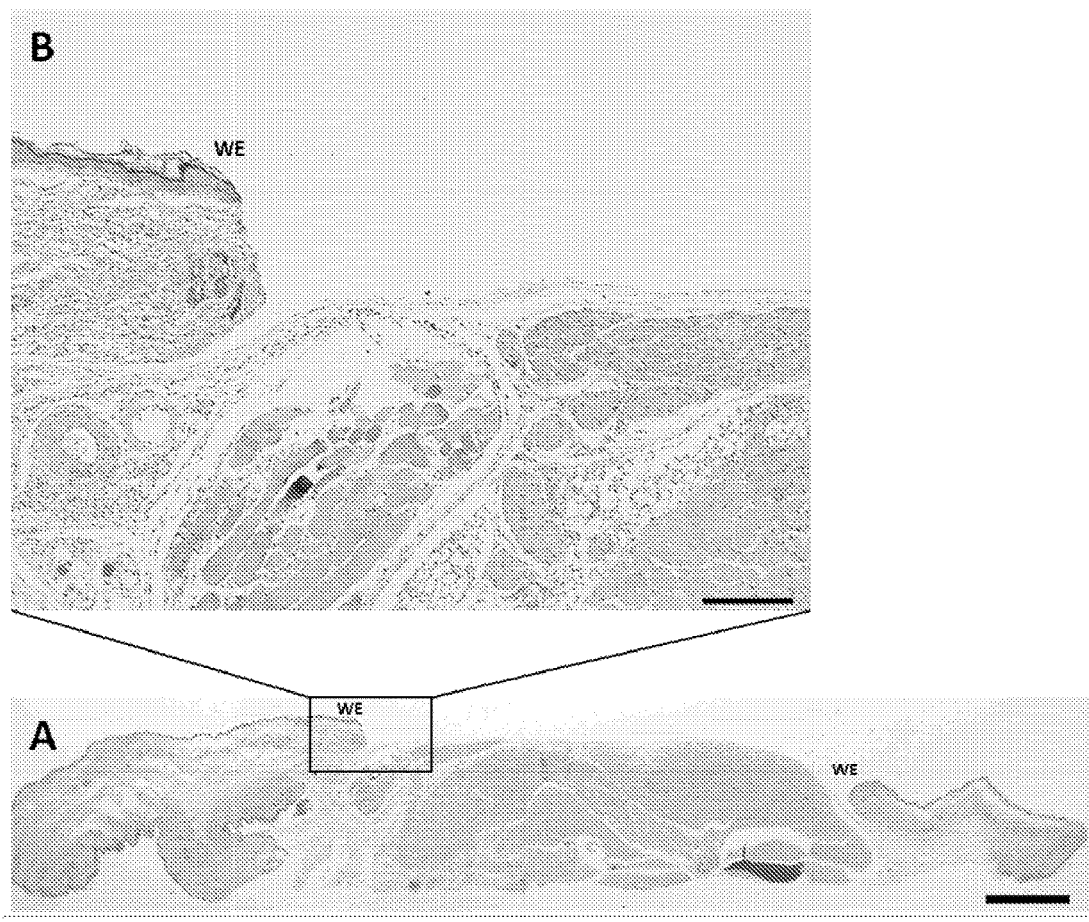
FIG. 10: (A) Hematoxylin and Eosin (H&E) stained sections of a typical mouse wound harvested on day 0. Hematoxylin is used to stain nuclei blue, while eosin stains cytoplasm and the extracellular connective tissue matrix pink. There is no epithelialization from the wound edge. Scale bar: 1 mm (B) Magnified portion of the wound section (scale bar: 200 μm.) which shows the wound edge and low inflammation ((low quantity of neutrophils (blue dots)) relative to day 1, 5 or 7 along with no reepithelialization or granulation. WE=wound edge.
Figure 11:
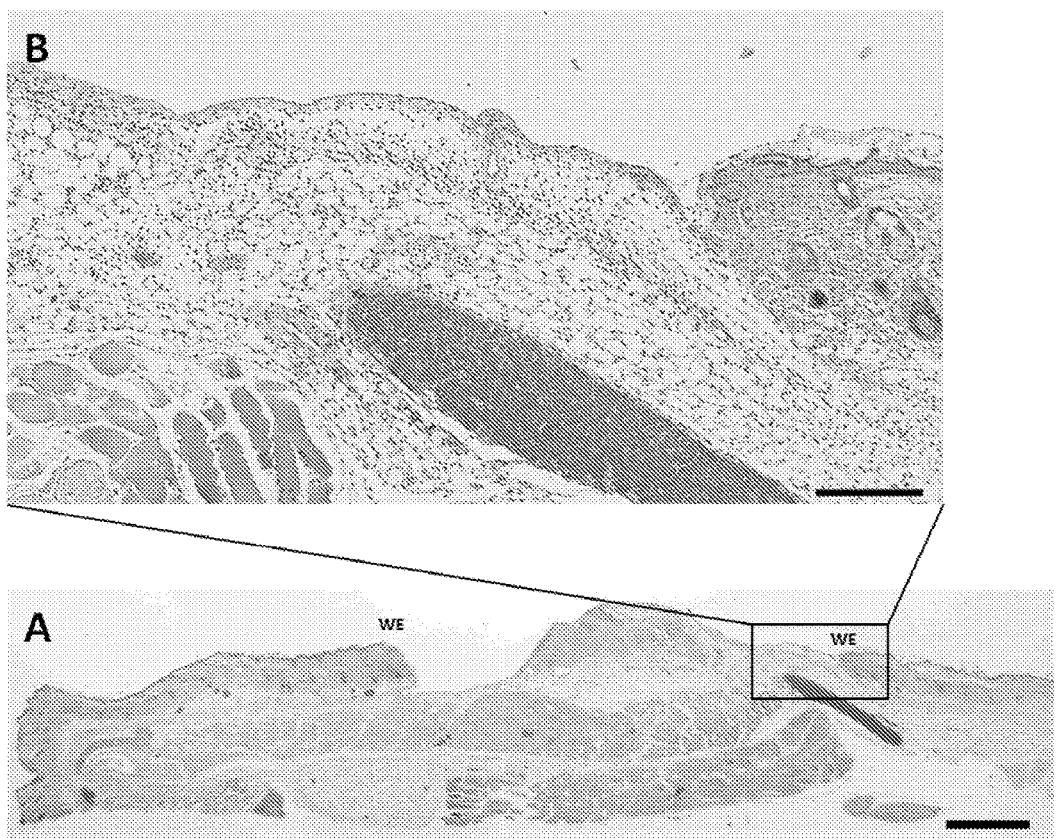
FIG. 11: (A) Hematoxylin and Eosin (H&E) stained sections of a typical mouse wound harvested on day 1. Scale bar: 1 mm. (B) Magnified portion of the wound section (scale bar: 200 μm.) which shows the epithelial edge of the wound and high inflammation (high quantity of neutrophils (blue dots)) relative to day 0. There is no re-epithelialization or significant granulation tissue formation. WE=wound edge.
Figure 12:
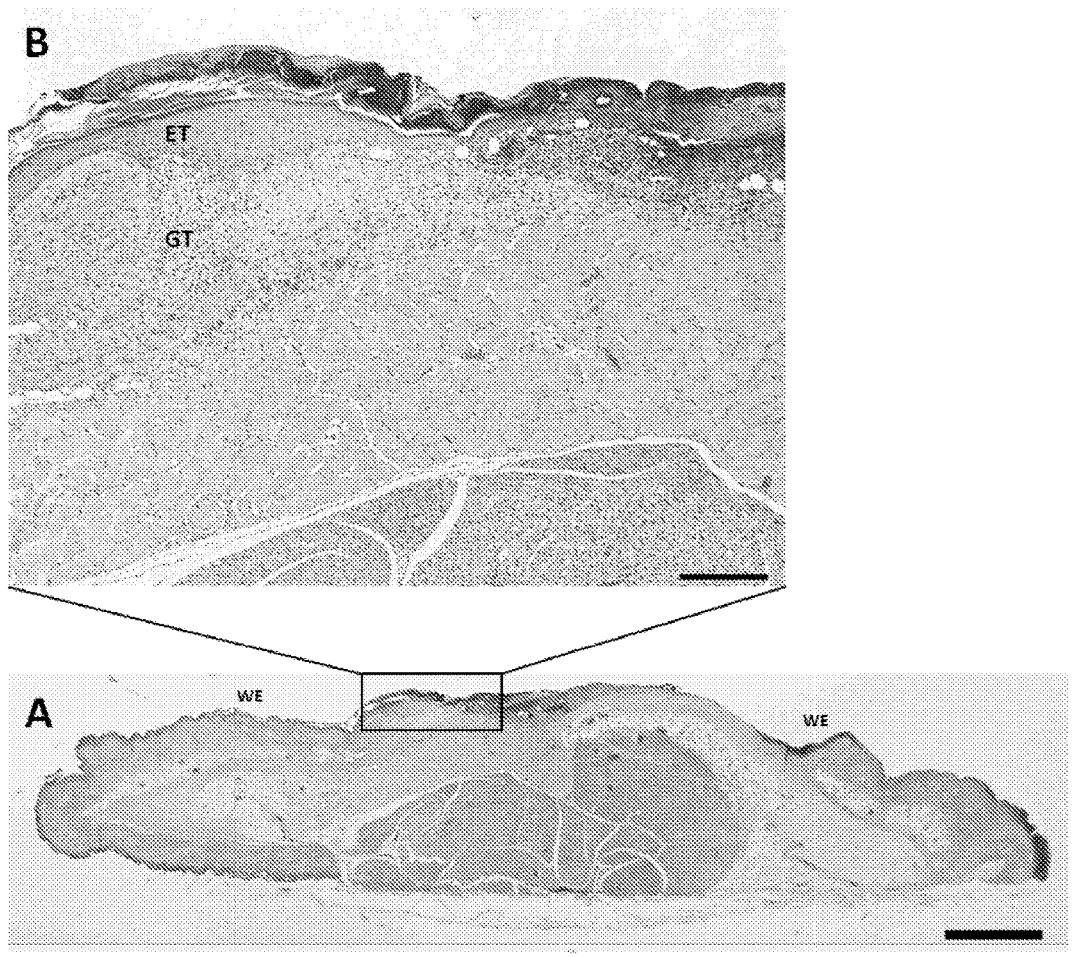
FIG. 12: (A) Hematoxylin and Eosin (H&E) stained sections of a typical mouse wound harvested on day 5. There has been significant epithelialization from the initial wound edge. Scale bar: 1 mm. (B) Magnified portion of the wound section (scale bar: 200 μm.) which shows high cellular activity (high quantity of neutrophils and fibroblasts (blue dots) and significant granulation tissue formation and reepithelialization). WE=wound edge, GT=granulation tissue, ET=epithelial tissue.
Figure 13:
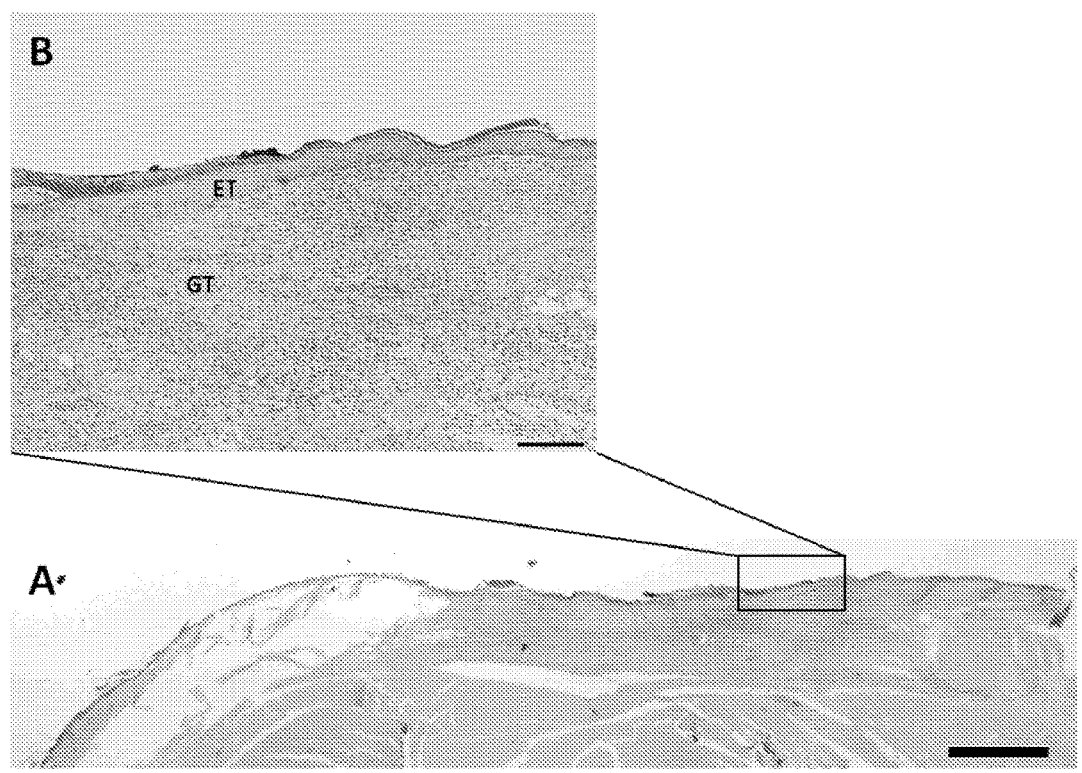
FIG. 13: (A) Hematoxylin and Eosin (H&E) stained sections of a typical mouse wound harvested on day 7. The wound is almost completely re-epithelialized. Scale bar: 1 mm. (B) Magnified portion of the wound section (scale bar: 200 μm.) which shows high cellular activity (high quantity of neutrophils and fibroblasts (blue dots)) and significant granulation tissue formation and re-epithelialization. WE=wound edge, GT=granulation tissue, ET=epithelial tissue.
Figure 15:
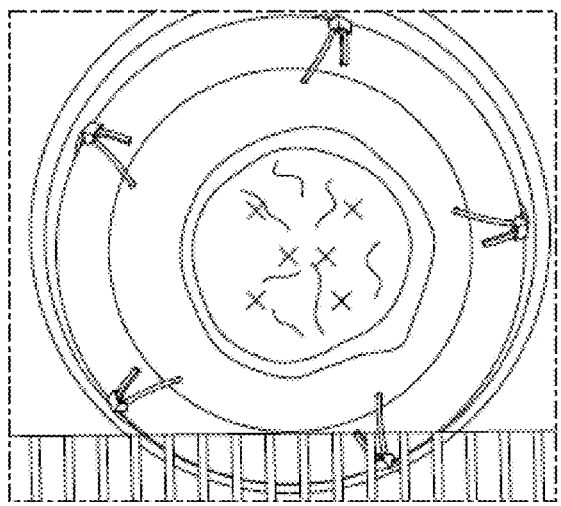
FIG. 15: Representative image denoting the different points across the surface of the wound bed (top left, top right, one or two from the centre, bottom left, bottom right) from where Raman spectra were collected. In general, these spectra, acquired from distinct spatial locations differed from each other reflecting spatial heterogeneity on the wound bed surface (see FIG. 9).

A confocal Raman microscope (Thermo Fisher Raman DXR) with a 10× objective (N.A. 0.25) and a laser wavelength of 532 nm (10 mW of power at sampling point) was used to collect spectra. The estimated spot size on the sample was 2.1 μm and resolution was 2.7-4 cm$^{-1}$. The confocal aperture used was a 25 μm pinhole and spectra between wavenumbers 500-3500 cm$^{-1}$ were collected. 5-6 spectra were collected from 6 different points across the surface of the wound bed (top left, top right, one or two from the centre, bottom left, bottom right, see FIG. 15) In general, these spectra, acquired from distinct spatial locations differed from each other reflecting spatial heterogeneity on the wound bed surface (see FIG. 9). The collection time for each spectrum was around 5 mins. Spectra were also collected for 7 pure components—bovine collagen (Sigma-Aldrich, St. Louis, Mo.), bovine elastin (Sigma-Aldrich, St. Louis, Mo.), hyaluronic acid (Lifecore Biomedical, Chaska, Minn.), fibronectin (Biomedical Technologies, Stoughton, Mass.), fibrin (Sigma-Aldrich, St. Louis, Mo.), human blood (from a volunteer) and triolein (Sigma-Aldrich, St. Louis, Mo.) for comparison to the spectra obtained from the wound beds. Background fluorescence was removed from all the spectra using polynomial fits and the spectra were normalized using OMNIC™ (Thermo Scientific) software.

Spectra collected from different points of a particular wound were averaged and this average spectrum was assumed to represent the entire wound in this study. The spectra representing individual wounds harvested on the same day were averaged again so that each day (day 0/1/5/7) was now represented by one spectrum (see FIG. 2) and an analysis of peak areas and peak locations was done for these averaged spectra. The spectral peaks were curve-fitted and analyzed for peak positions and peak areas using Fityk (34). Multivariate Factor Analysis was performed on all spectra representing individual wounds using XLSTAT version 2013.1.02 (MS Excel add-in) to express the spectra as a weighted sum of 3 'factor score spectra' with the weights termed as 'factor loadings'. Factor scores were also normalized and scaled to convert them into 'factor score spectra' which were correlated with real spectra belonging to the 7 different wound bed constituents using Non-Negative Least Squares (NNLS) analysis using MATLAB (v. R2012b). For this analysis, $R^2$ (coefficient of multiple correlation)>0.9 for all factor score spectra. A Ryan-Einot-Gabriel-Welsch Q multiple comparison test (REGWQ test—ANOVA) for determining the significance of differences (confidence interval: 95%) between sets of factor loading values for wounds on different days was also performed and the results are presented in Table 4.

Multivariate Factor Analysis (MFA) of Raman Spectra

Figure 8:
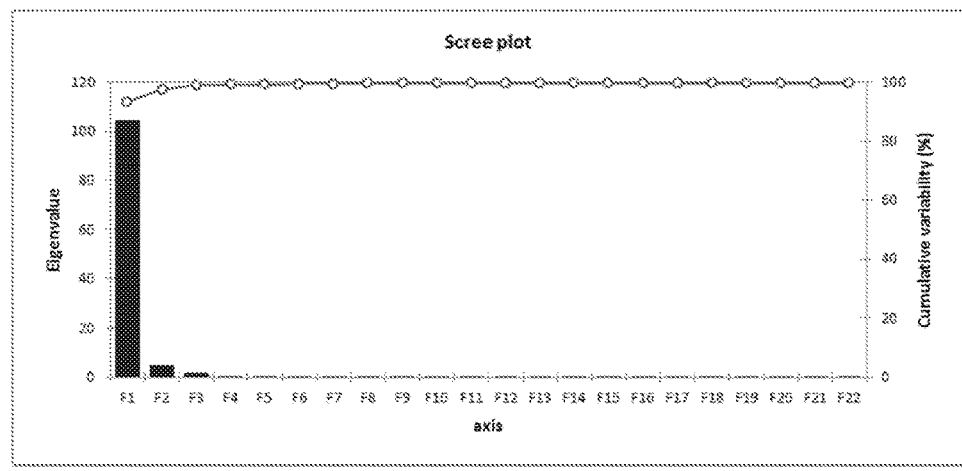
FIG. 8: Scree plot showing eigenvalues for the correlation matrix of the spectral dataset. Cumulative variability for Factor 3 is 98.95%.

Consider a spectral dataset (N×P) containing N spectra (representing N wounds) across a range of P wavenumbers. As the first step of MFA, a correlation matrix (N×N) was formed from this spectral dataset and an eigenanalysis is performed to extract N eigenvectors and their eigenvalues from this matrix. The first three eigenvectors (having eigenvalues>1 (Kaiser-Guttman rule (35))) were considered for further analysis and they could express 99% of the variability in the spectral dataset in terms of the eigenvalues (see FIG. 8 (scree plot)). The factor score matrix (which contain 3 vectors (factor score spectra)) and the factor loading matrix could now be obtained from the eigenvector matrix and the original data matrix by simple matrix operations (36). The original spectral data could be reproduced as the linear, weighted sum of factor score spectra with the factor loadings acting as the weights. Thereafter, we employed an oblique rotation method (Promax rotation (37)) on the initial factor axes to increase the simplicity of interpretation (38), make each variable (wound spectrum) identify with one or a small proportion of the factors (and thus enable clustering of similar variables on basis of their factor loadings)(35), spread the variance across factors more evenly (35) and generate an invariant factor solution (35) (that does not depend on the particular mix of variables involved and is generalizable across experiments). As a result of employing Promax rotations, the resulting factor score spectra were also able to resemble non-negative, 'real' spectra that could be assigned as spectral signatures for the different stages of healing (based on subsequent non-negative least squares fitting with basis spectra of the wound bed constituents) and thus model real, physical phenomena (wound healing). We employed Promax rotation of the factor axes with a power of 4. The factor loadings reported are factor 'pattern' loadings which represent the unique contribution of each factor to each variable (35). After oblique rotations of the factor axes, the factors are no longer orthogonal and are correlated with each other which is consistent with our hypothesis that the factors model the levels of biochemical constituents associated with the stages of wound healing which are correlated with each other.

Analysis of Averaged Raman Spectra of Mice Wounds on Day 0, 1, 5 and 7

Based on prior experience with histopathologic analysis of mice wounds used in other experiments in our animal laboratory, we chose 4 different time-points (0, 1, 5 and 7 days) at which to collect Raman spectra from the wounds in order to probe the biochemical changes that occur on a healing wound as it progresses through different stages (homeostasis, inflammation, granulation/proliferation). FIG. 1 shows sample images of splinted mice wounds obtained on the different days. Only minor differences can be seen in their gross appearance, except for a marked reduction in the wound size on the 7$^{th}$ day. Histopathological scores for inflammation and granulation were consistent with the wounds at different times corresponding to different stages of healing (see FIGS. 10-13 and Table 3).

Figure 2:
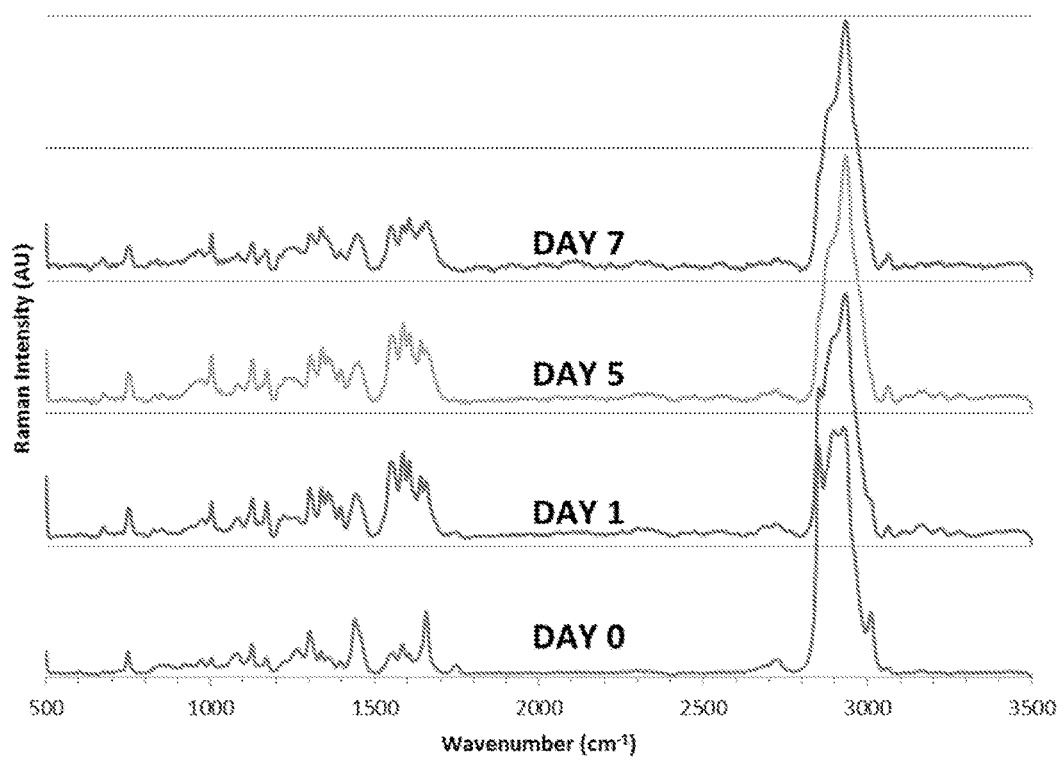
FIG. 2: Averaged Raman spectra of mice wounds on day 0 (n=30), day 1 (n=36), day 5 (n=23) and day 7 (n=23).

Raman spectra were collected from multiple points on each wound (see FIG. 9 for spatial variation in Raman spectra in a wound) and averaged so that each wound was represented by one spectrum. For analysis of peak locations and areas, these spectra representing individual wounds were averaged again for each time-point (0/1/5/7 day). FIG. 2 shows the Raman spectra for different time points and Table 2 summarizes peak locations and areas. The prominent Raman peaks in the spectra can be grouped into 3 categories: (i) peaks related to the strong amide I (WN: 1620-1680 cm$^{-1}$) and amide III (WN: 1220-1270 cm$^{-1}$) vibrational modes for the peptide backbone, which indicate different protein secondary structures (39, 40), (ii) peaks that correspond to specific side-chains for specific amino-acids (WN: 674, 749, 785, 826, 851, 1003, 1030, 1172, 1338, 1360, 1398, 1585, 1606 cm$^{-1}$) making up the proteins (41), and (iii) peaks corresponding to the —CH stretching region at higher wavenumbers (WN: 2700-3100 cm$^{-1}$) which indicate relative quantities of total protein and lipid (42-44). From these groupings, we make three observations. First, the decrease in areas for multiple peaks corresponding to α-helical secondary structure (WN: 1267, 1655 cm$^{-1}$) and a simultaneous increase in areas for peaks representing β-sheets (WN: 1223, 1623, 1638 cm$^{-1}$) and random coils (WN: 1244, 1671 cm$^{-1}$) across the Amide I and Amide III vibrational regions indicate the deposition of new proteins on a wound bed which initially contained residual ECM collagen (α-helical). Fibrin, collagen type III, fibronectin, elastin, hyaluronic acid and cells and proteins in blood plasma are generally the major constituents of granulation tissue that forms on the wound bed in the course of healing. Fibrin is a key protein forming the blood clot and granulation tissue and has high non-helical (β-sheet+random coil~80%) secondary structure content (45-48). Fibronectin is another key protein that form the provisional matrix on a wound during the first week of wound repair (49, 50) and it also has a high content (~80%) of β-sheets (WN: 1637, 1679, 1225 cm$^{-1}$) in particular (51). Second, most peaks which correspond to amino acids (WN: 674, 749, 785, 1003, 1360 cm$^{-1}$) are observed to have a 2-4 fold increase in area and this is again consistent with protein accumulation on the wound bed. Third, peak areas which are lipid specific (WN: 2852, 2933, 3010 cm$^{-1}$) are reduced 1-4 fold with time and ones which are protein-specific (WN: 2897, 2968, 3062 cm$^{-1}$) are increased 1-3 fold. This result is consistent with subcutaneous fat (that is exposed when a full-thickness wound is created) being overlaid with granulation tissue. We note, however, that many peak locations suffer from redundancy of assignment (as seen in Table 2) and individual peaks can't be assigned to specific ECM proteins on the wound bed with certainty. Consequently, we sought to employ multivariate statistical methods which can distinguish between wound spectra based on aggregated differences across a wide wavenumber range.

Figure 3:
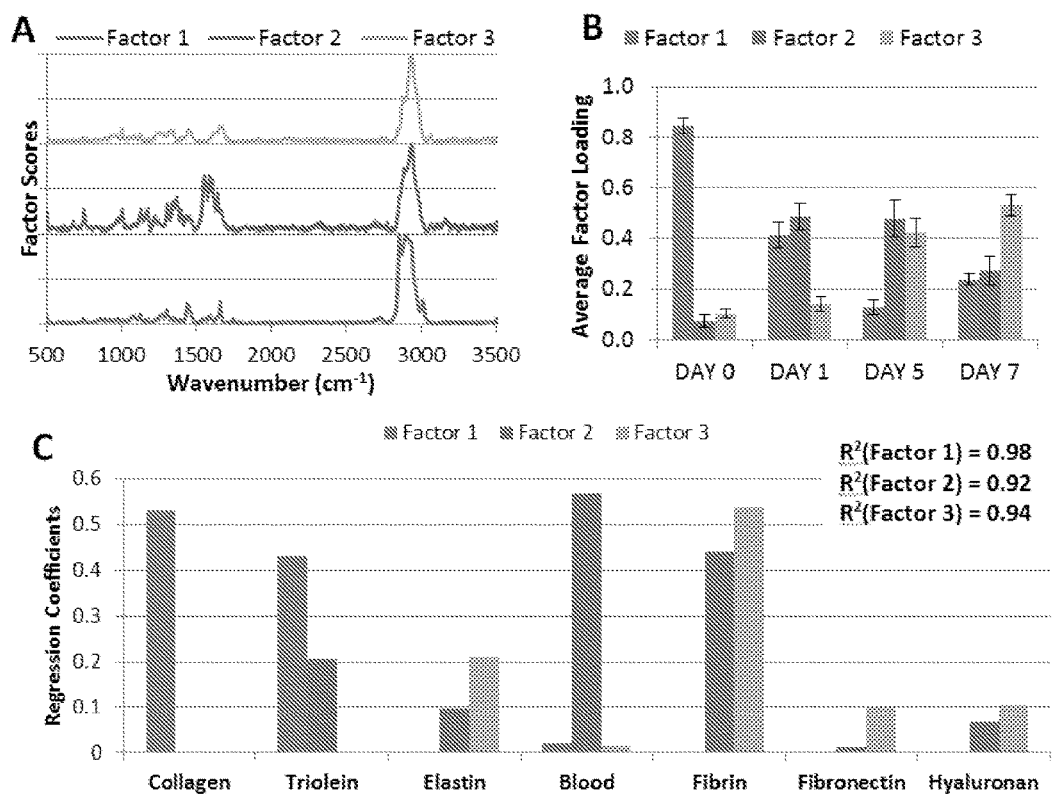
FIG. 3: (A) Factor score spectra (normalized and scaled) from MFA (B) Average factor loadings from MFA (normalized and scaled). Error bars indicate±SEM. (C) Standardized regression coefficients of model basis spectra of wound bed constituents for the factor score spectra.

Multivariate Factor Analysis (MFA) of the Spectral Dataset and Non-Negative Least Squares (NNLS) Fitting of Factor Score Spectra We used Multivariate Factor Analysis (MFA) to decompose the spectrum representing each individual wound as a linear weighted sum of 'factor scores' whose scalar weights are termed as 'factor loadings'. FIG. 3A shows the factor scores (scaled and normalized) obtained from MFA plotted against wavenumber. FIG. 3B shows averaged factor loading values for all wounds harvested at a particular time-point and a distinct pattern of factor loading values can be observed for each time-point (values sum to 1 at each time-point) which in turn corresponds to different stages of wound healing. While factor 1 loading is seen to decrease with time, factor 2 and factor 3 loadings are seen to increase with time. We speculated that factor 1 is likely correlated with the fresh state of a wound whereas factors 2 and 3 probably represent the accumulation of cells and proteins that are associated with inflammatory stage and deposition of granulation tissue respectively. Consistent with our hypothesis, FIG. 3B depicts that the average loading value for factor 1 is reduced by 50% (from 0.84±0.03 to 0.41±0.05) and factor 2 is increased 6-7 fold (from 0.07±0.02 to 0.48±0.05) between day 0 and day 1. On day 5, the factor 1 loading value is reduced even further to 15% of its initial value (from 0.84±0.03 to 0.13±0.03), factor 2 remains the same and factor 3 loading increases 4-fold (from 0.1±0.02 to 0.42±0.06). The day 7 factor loadings were not found to be significantly different from day 5 (for details, refer to Table 4) except for a decrease in factor 2 loadings (to 0.27±0.05).

Figure 7:
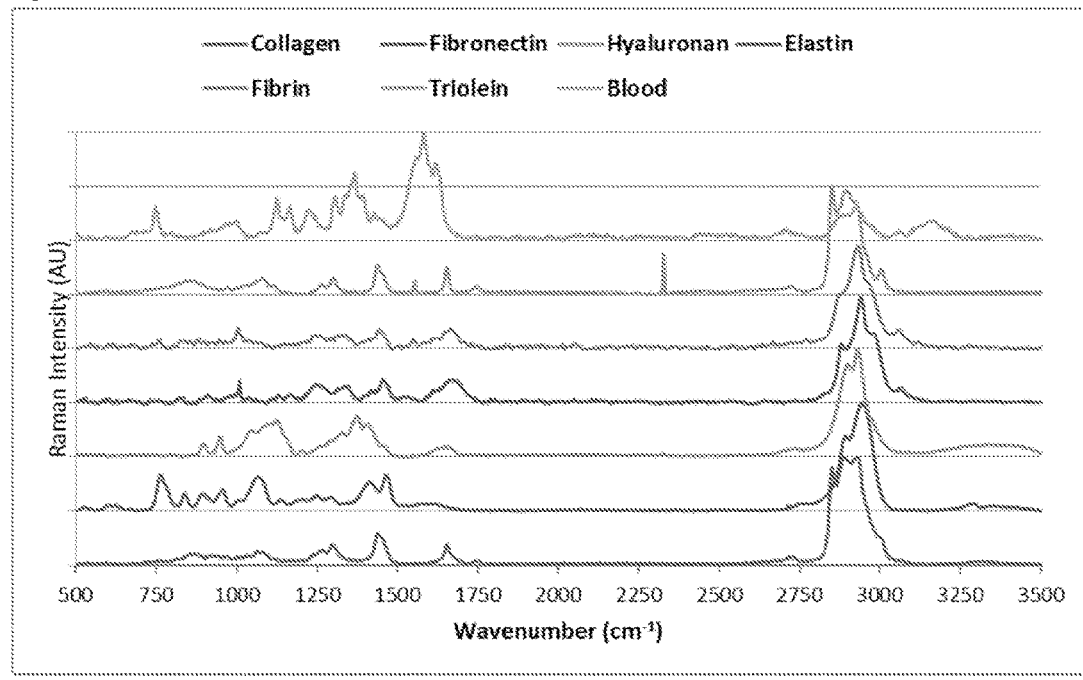
FIG. 7: Basis spectra for wound bed constituents used for NNLS fitting of factor score spectra. Raman bands and relative intensities are presented in Table S3.

Based on the above observations, we sought to determine if it was possible to associate each factor score spectrum to real wound bed constituents that are typically present during the course of healing. Our model consisted of basis spectra from 7 major wound bed constituents (see FIG. 7 for basis spectra, Table 5 for their Raman bands) and the factor score spectra could be depicted as an aggregate of these basis spectra with a high degree of fit ($R^2$ values >0.90) using Non-Negative Least Squares (NNLS) analysis. FIG. 3C shows the regression coefficients (RC) for the basis spectra which collectively sum to 1 for each factor score spectrum. FIG. 3C indicates that Factor 1 score spectrum has strong contributions from collagen (RC: 0.53) and triolein (RC: 0.43; a triglyceride that mimics subcutaneous fat (52))—components that correlate strongly to the fresh state of a full-thickness wound bed. Factor 2 score spectrum has high contributions from blood (RC: 0.57, which contains inflammatory cells) and fibrin (RC: 0.44)—components that represent inflammation on the wound bed as healing progresses and minor contributions from elastin (RC: 0.1), hyaluronic acid (0.06) and fibronectin (RC: 0.01). Factor 3 score spectrum has strong contributions from fibrin (RC: 0.53), elastin (RC: 0.2), hyaluronic acid (RC: 0.1) and fibronectin (RC: 0.1) all of which are key components of granulation tissue on the wound bed and reflect a high proclivity of the wound towards cell proliferation which would lead to wound closure.

Distinction Between Individual Wounds on Basis of Factor Loading Values

Figure 4:
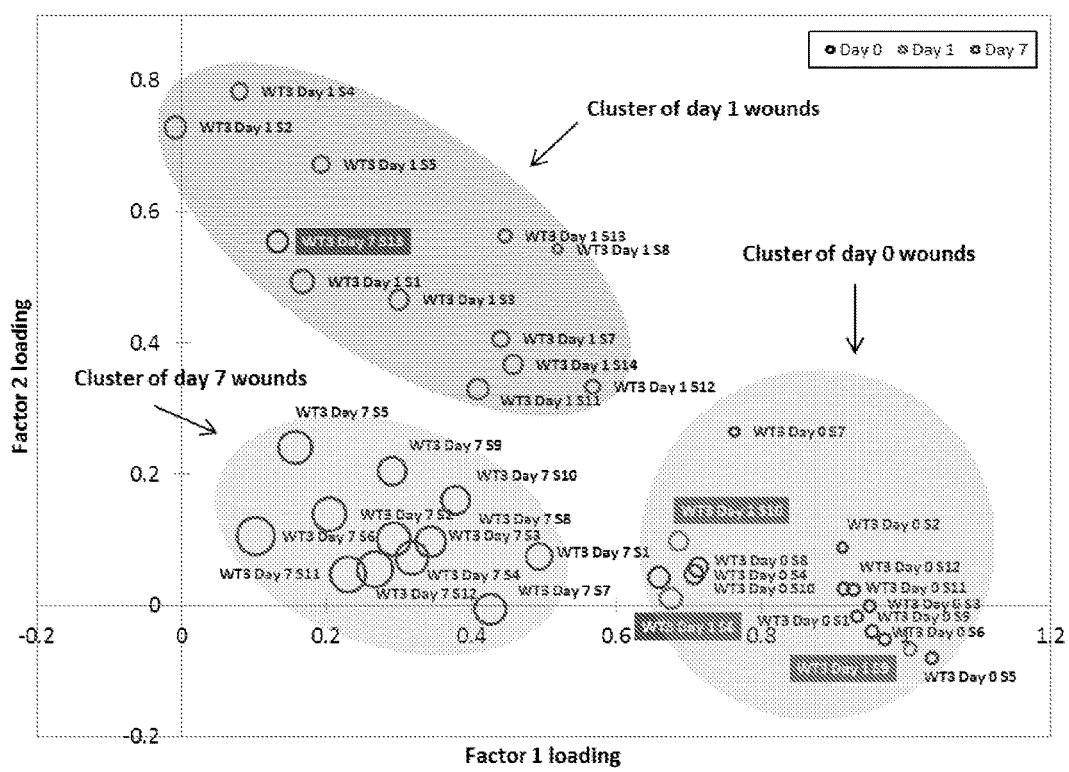
FIG. 4: Wounds cluster around three sets of factor loadings (based on Raman spectroscopic characterization) which represent different stages of healing. The axes represent factors 1 and 2 while the third factor is represented by the size of the circles. The wounds represented in this graph were from a single experiment (WT3) involving 12-14 wounds (S1 to S14; created in 6-7 mice) that were characterized at each time-point (Day 0/Day 1/Day 7). Outliers indicate slowly healing wounds and are marked with red boxed labels. All the wounds were analyzed using histopathology.
Figure 5:
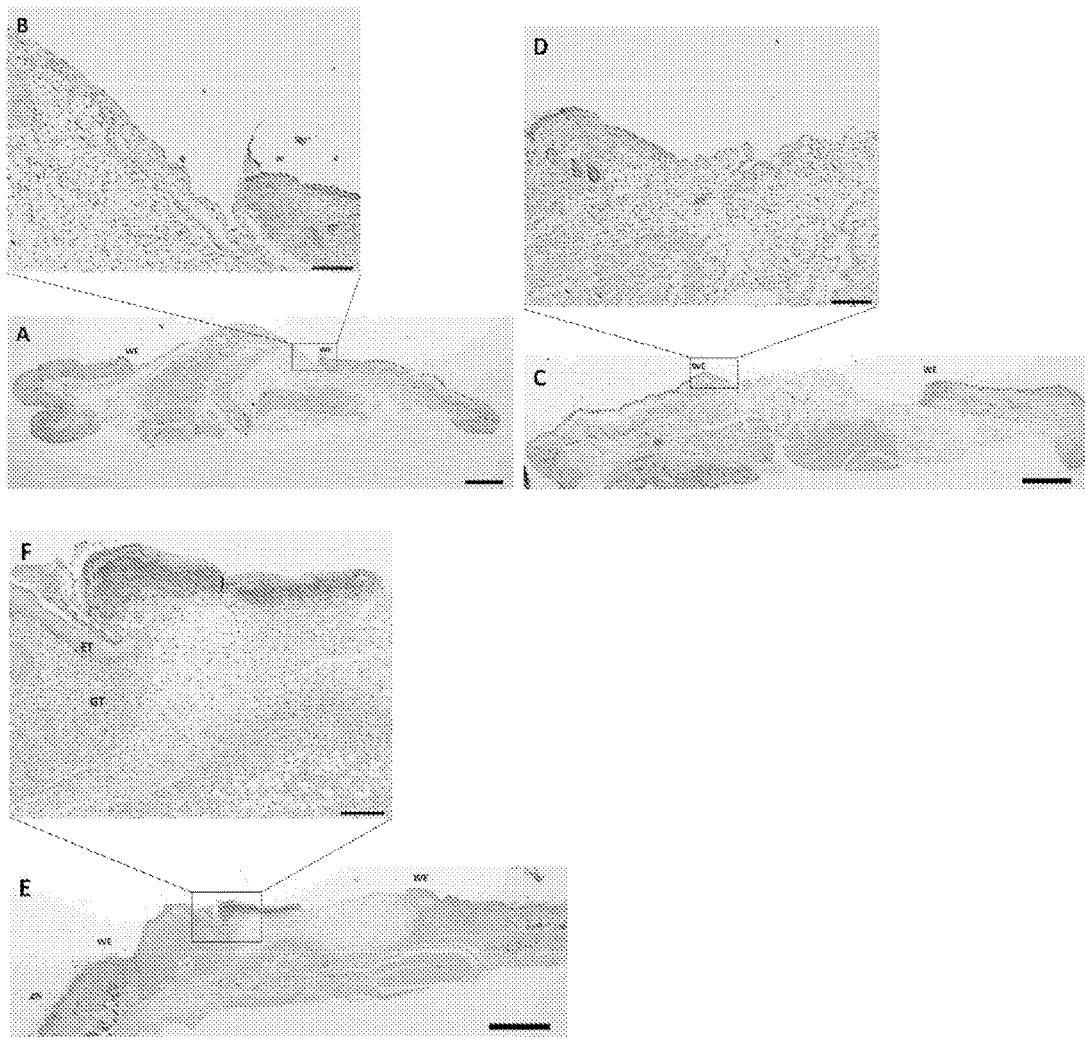
FIG. 5: Hematoxylin and Eosin (H&E) stained sections of wounds. Hematoxylin is used to stain nuclei blue, while eosin stains cytoplasm and the extracellular connective tissue matrix pink. (A) H&E stained section of wound (WT3 Day 1 S6) indicated as an outlier by Raman spectral analysis in FIG. 4. The appearance of the wound is similar to a day 0 wound. Scale bar: 1 mm. (B) Magnified portion of the wound section (scale bar: 200 µm.) shows a relatively lower level of inflammatory cells (blue dots) than a typical day 1 wound (refer FIG. 11). (C) H&E stained section of wound (WT3 Day 1 S9) indicated as an outlier by Raman spectral analysis in FIG. 4. The appearance of the wound is similar to a day 0 wound. Scale bar: 1 mm. (D) Magnified portion of the wound section (scale bar: 200 µm.) shows a relatively lower level of inflammatory cells (blue dots) than a typical day 1 wound (refer FIG. 11). (E) H&E stained section of wound (WT3 Day 7 S13) indicated as an outlier by Raman spectral analysis in FIG. 4. The appearance of the wound indicates delayed healing relative to a typical day 7 wound. Scale bar: 1 mm. (F) Magnified portion of the wound section (scale bar: 200 µm.) shows a higher level of inflammatory cells (blue dots), but a relatively lower level of granulation tissue formation than a typical day 7 wound (refer FIG. 13). WE=wound edge, GT=granulation tissue, ET=newly formed epithelial tissue.
Figure 14:
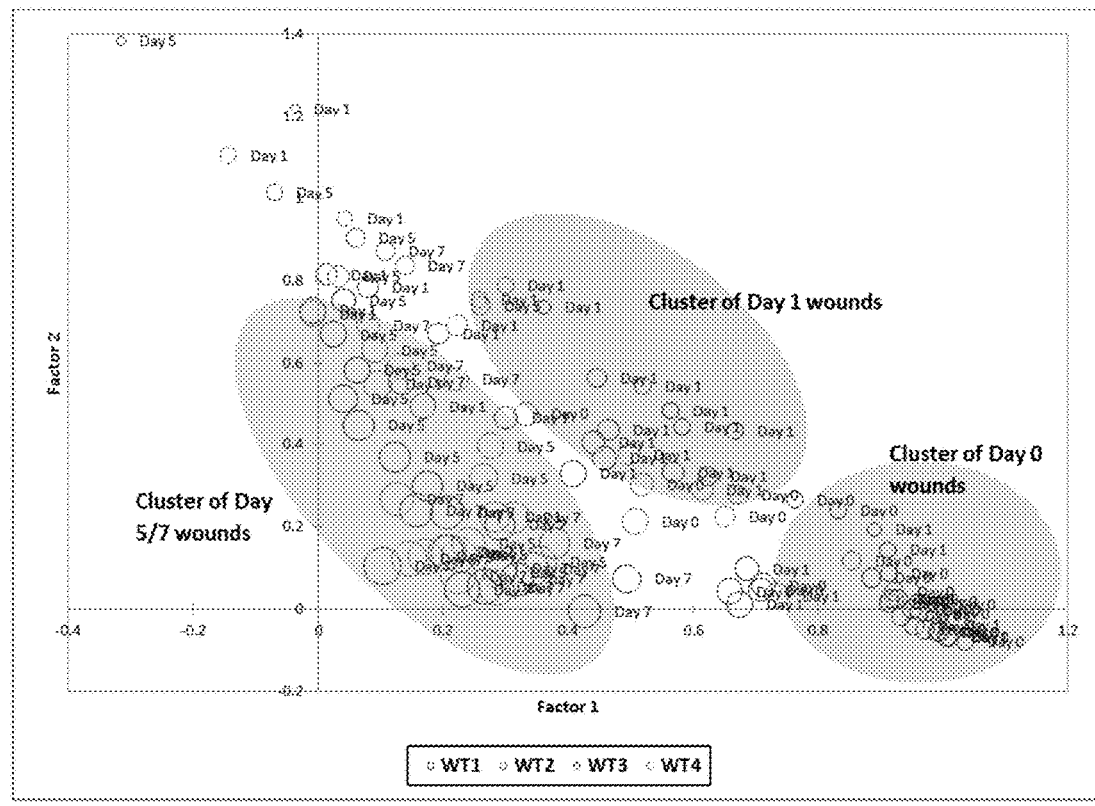
FIG. 14: Graph which shows the broad clustering of wounds around three sets of factor loadings (based on Raman spectroscopic characterization) which represent different stages of healing. Note that the third factor is represented by the size of the circles which also varies significantly. All the 112 wounds which were part of repeat experiments (batches of mice WT1-WT4) are represented in this graph.

MFA enables a simple way to quantify the variability among the different spectra by comparing factor loading values. Here we show that this can be used to distinguish between individual wounds in different healing stages. FIG. 4 shows the clustering of wounds (from the experiment on the batch of mice 'WT3') which belong to similar stages of healing based on their factor loadings. They are plotted graphically in a 3D graph where the axes represent 2 of the factors and the size of circles belonging to different wounds represents the third factor. While all wounds harvested on day 0 were similar to each other in their spectra and hence had loading values close to each other, 4 wounds belonging to later time-points (day 1 and day 7) behaved as 'outliers' whose loading values corresponded to earlier time points (day 0 or day 1 respectively) and are highlighted in red in FIG. 4. Specifically, the outlier wound for the set of wounds harvested on day 7 (WT3 Day 7, S13) has low factor 1 and factor 3 loading values (0.132 and 0.355 respectively), but a high factor 2 loading value (0.554). We confirmed this observation with histopathologic imaging of the wound sections (see FIGS. 5E and 5F) which also shows the 'outlier' wound to be impaired in its healing in terms of granulation scores and re-epithelialization (which we have associated earlier with factor 3 on basis of NNLS fitting), but has high inflammation (associated with factor 2). Again, three wounds were outliers among those harvested on Day 1 (WT3 Day 1 S6, S9 and S10) with high factor 1 loading values and low factor 2 and 3 loading values. This is consistent with histopathologic images of sections from 2 out of the 3 wounds (WT3 Day 1 S6 and S9; see FIG. 5A-5D) which indicate a relatively low inflammation score than typical day 1 wounds and an overall appearance similar to day 0 wounds. The clustering of wounds on the basis of their healing states was broadly consistent across the different batches of mice used in repeat experiments (see FIG. 14).

When a full-thickness wound is created in mice initially, subcutaneous fat and residual ECM collagen is exposed and forms the initial wound bed. Significant biochemical changes occur on the wound-bed within the first day of wounding, when hemostasis is established and an inflammatory response is mounted (53). As a result, a provisional matrix principally made up of fibrin and fibronectin is deposited on the wound bed which is permeated with inflammatory cells (neutrophils, macrophages) and burst platelets from blood. While this wound bed activity is not apparent based on gross physical appearance of the wounds alone (see FIGS. 1A and 1B), it is evidenced in the notable differences in factor loading values obtained from Raman spectra between day 0 and day 1 (see FIG. 3B)—a decrease in factor 1 (associated with subcutaneous fat and residual ECM collagen) by 50% and an increase in factor 2 (associated principally with fibrin and blood) by 6-7 fold. The provisional matrix so formed is subsequently infiltrated by fibroblasts and remodeled into granulation tissue (which contains wound bed constituents such as hyaluronic acid, fibronectin, elastin and collagen type III) and inflammation subsides. This activity is manifested in the changes to factor loading values as well—factor 2 decreases by day 7, factor 3 (associated principally with fibrin, fibronectin, hyaluronan and elastin) increases progressively, and there is an increase in factor 1 (associated with collagen) also by day 7. Thus the 3 factors used to describe the spectra in our study successfully permit identification of the phase of healing for a particular wound on the basis of changes in quantities of underlying biochemical components. However, we note that NNLS fitting of factor score spectra with basis spectra can be improved further and higher $R^2$-values could potentially be achieved by increasing the number of basis components in our model.

The results presented in FIG. 4 also indicated that wounds in different individual mice with different extents of progress in their healing formed distinct clusters on basis of their factor loading values. The cluster analysis also identified 'outlier' wounds which we hypothesized to indicate impairment in their healing, as murine wound healing progress is known to vary across individual mice (54). Three out of 4 outlier wounds so identified could be associated with an altered histopathologic profile (see FIG. 5). We note that one histological section taken from the entire wound may not always be representative. Also, spectra were collected from 5-6 different random areas (size~10 μm$^2$) on each wound and averaged to represent the entire wound which was much larger (size~20 mm$^2$) Our approach was designed for rapid collection of spectra from each wound due to the large number of wounds considered in our experiments, and it is noteworthy that the factor loading values could still indicate the progress in healing of the wounds very well (see FIG. 3B). However, the spatial heterogeneity of a wound is also an important aspect of healing, and a Raman imaging approach could be used to create a map of biochemical features. This approach may lead to practical advantages in the clinic by informing selective therapeutic interventions such as discrete partial wound debridements that selectively target areas of impaired healing while not disturbing areas of a wound that are progressing satisfactorily. Finally, we comment that the determination of inflammation and granulation tissue formation on the basis of histopathologic scores can be arbitrary due to the nature of evaluation of histopathologic images being subjective and qualitative (12, 13). In contrast, our approach gives a semi-quantitative measure of healing progress in terms of factor loading values which could be an objective way to determine inflammation and granulation in wounds.

Figure 6:
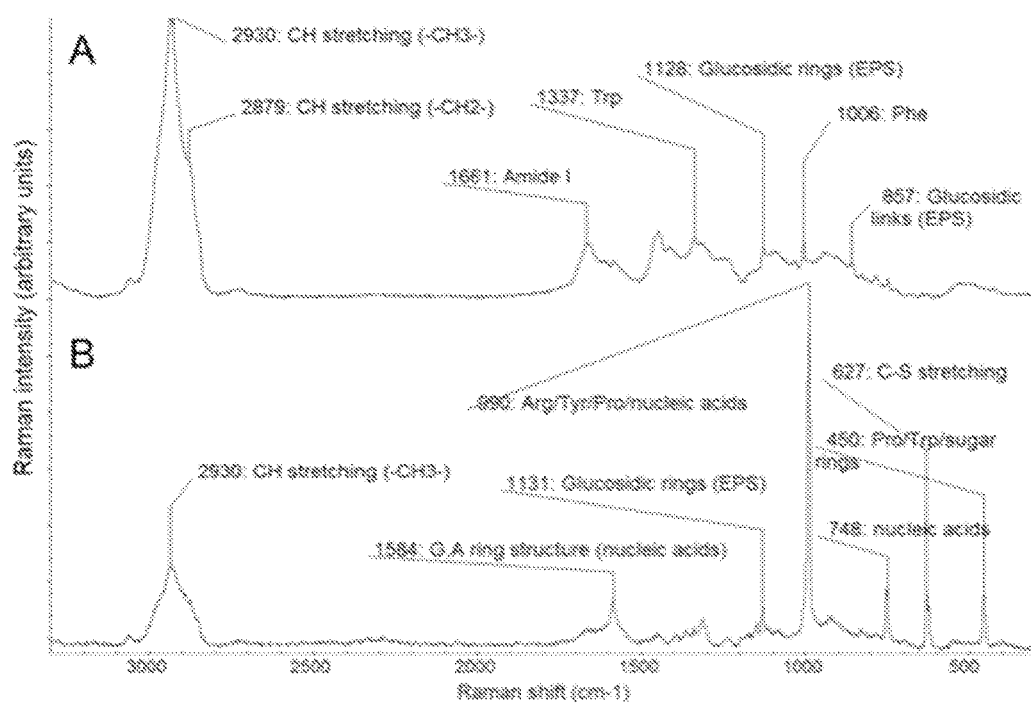
FIG. 6: Raman spectra and peak assignments of different bacterial biofilms formed on glass in vitro (A) *Staphylococcus aureus* (B) Pseudonomas aeruginosa.

In summary, we have shown that progress of healing of wounds can be accurately evaluated in terms of biochemical changes occurring on the wound bed surface in a simple, non-invasive manner that combines Raman spectroscopy and spectral analysis. Specifically, we could quantitatively track wound healing progress in terms of key parameters such as inflammation and granulation with the help of MFA/NNLS in mice wounds and also distinguish between individual wounds at different stages of healing. The results presented in this paper enable future studies of the biochemistry of a broad range of wound bed models (animal models, chronic wounds, wounds with biofilms). In preliminary work, we have collected Raman spectra of bacterial biofilms in vitro (see FIG. 6) that showed distinct, sharp Raman peaks which can be assigned specifically to biofilm components. Also, the biofilms of different bacterial strains differ significantly (compare FIG. 6A to 6B). These results suggest strongly that biofilms will be easily identified by Raman spectroscopy in vivo. Overall, our results also offer substantial potential for translation to clinic, where wounds would be evaluated non-invasively by handheld Raman spectrometers in conjunction with spectral analysis.

TABLE 2

Summary of prominent peak locations and peak areas in averaged Raman spectra of wounds harvested on day 0, 1, 5 and 7 whose assignments are based on references 41, 42, 55 and 56).

| Peak Location (cm$^{-1}$) | Peak Area (AU) | | | | Assignment |
|---|---|---|---|---|---|
| | Day 0 | Day 1 | Day 5 | Day 7 | |
| 674 | 0.76 | 2.21 | 3.50 | 4.20 | Cys/Met (v(C—S) stretching) |
| 749 | 1.53 | 2.76 | 3.92 | 4.64 | Phe/Trp (v(C—C—O) (aromatic)) |
| 785 | — | 2.53 | 2.69 | 2.67 | His |
| 826 | 0.26 | 0.69 | 1.37 | 1.72 | Tyr doublet (ring breathing - para-benzene) |
| 851 | 2.01 | 2.77 | 1.51 | 2.37 | |
| 940 | 1.71 | 3.14 | 4.29 | 4.20 | Glu (COO- deformation) |
| 972 | 2.36 | 3.02 | 4.67 | 3.66 | cytosine/N-acetylglucosamine (hyaluronan)/Serine/ |
| 1003 | 2.05 | 2.54 | 3.92 | 3.82 | Phe (aromatic ring breathing) |
| 1030 | 0.97 | 1.10 | 2.53 | 2.90 | Val/Phe/Pro |
| 1080 | 5.12 | 5.24 | 5.85 | 2.43 | His/Pro/Triolein (C—N stretching - proteins/C—C stretching - triolein) |
| 1128 | 2.08 | 3.97 | 4.36 | 3.05 | N-acetylglucosamine (hyaluronan)/adenine/Gly/Val |
| 1148 | 0.77 | 1.37 | 1.30 | 1.31 | N-acetylglucosamine (hyaluronan) |
| 1172 | 1.91 | 3.54 | 3.82 | 1.84 | His/Pro |
| 1206 | — | 1.56 | 1.76 | 2.15 | Tyr/Trp/hyaluronan |
| 1223 | 0.98 | 2.61 | 3.18 | 1.48 | Amide III (β-sheet) |
| 1244 | — | 1.04 | 1.90 | 2.62 | Amide III (random coils) |
| 1267 | 6.96 | 2.90 | 4.05 | 2.51 | Amide III (α-helix) |
| 1338 | 2.92 | 4.12 | 8.28 | 2.99 | Trp doublet |
| 1360 | 1.42 | 3.43 | 3.00 | 4.02 | |
| 1398 | 1.99 | 2.20 | 4.47 | 4.93 | Gly/Val/Uracil/Thymine |
| 1442 | 8.38 | 10.16 | 11.17 | 9.48 | C—H deformation in proteins/lipids |
| 1550 | 2.61 | 9.76 | 11.22 | 8.86 | Trp related mode or Amide II (II (60% N—H bend and 40% C—N stretch) |
| 1585 | 4.16 | 9.63 | 5.77 | 2.67 | Phe/Trp |
| 1606 | 0.66 | 3.46 | 5.63 | 5.77 | Phe/Tyr (phenolate related vibrational activity) |

TABLE 2-continued

Summary of prominent peak locations and peak areas in averaged Raman spectra of wounds harvested on day 0, 1, 5 and 7 whose assignments are based on references 41, 42, 55 and 56).

| Peak Location ($cm^{-1}$) | Peak Area (AU) | | | | Assignment |
|---|---|---|---|---|---|
| | Day 0 | Day 1 | Day 5 | Day 7 | |
| 1623 | 1.22 | 3.21 | 2.35 | 1.47 | Amide I (β-sheet) |
| 1638 | 1.35 | 3.89 | 5.82 | 4.52 | Amide I (β-sheet) |
| 1655 | 4.28 | 3.31 | 2.15 | 3.09 | Amide I (α-helix) |
| 1671 | 0.44 | 3.02 | 3.60 | 2.88 | Amide I (random coils). Overlap with beta-sheets. |
| 1688 | 1.04 | 1.58 | 2.22 | 2.03 | Amide I (β-turns) |
| 2852 | 25.84 | 7.81 | 9.54 | 6.64 | C—H stretching symmetric (—CH2—). Lipid-specific |
| 2897 | 30.37 | 51.00 | 34.00 | 27.78 | C—H stretching symmetric (—CH2—). Protein-specific |
| 2933 | 37.98 | 23.00 | 23.00 | 27.53 | C—H stretching asymmetric (—CH3—). Lipid Specific |
| 2968 | 10.43 | 16.63 | 27.00 | 24.60 | C—H stretching asymmetric (—CH3—). Protein Specific |
| 3011 | 8.88 | 6.14 | 4.63 | 3.42 | =C—H stretch of =CHR or =CH2 groups (unsaturated lipids) |
| 3062 | 1.20 | 1.61 | 3.20 | 4.24 | C—H stretch aromatic amino acids (proteins) |

TABLE 3

Re-epithelialization lengths, inflammation and granulation scores from histopathologic analysis of the sets of wounds 'WT2', 'WT3' and 'WT4'. The progressive increase in inflammation (score scale: 0 (lowest)-4 (highest)), re-epithelialization (in mm.) and granulation tissue scores (scale: 0 (lowest)-4 (highest)) in wounds at later time-points confirms the advancement of the wounds through different stages of healing. NWPOS: No wound present on slides. Some wound sections were desiccated or damaged and therefore could not be analyzed on the histopathologic slides.

| Sample | Re-epi (mm) | Inflammation | Granulation |
|---|---|---|---|
| WT2 Day 0 S1 | 0 | 0 | 0 |
| WT2 Day 0 S2 | 0 | 0 | 1 |
| WT2 Day 0 S3 | 0 | 0 | 0 |
| WT2 Day 0 S4 | 0 | 0 | 0 |
| WT2 Day 1 S1 | 0 | 0 | 0 |
| WT2 Day 1 S2 | 0 | 2 | 0 |
| WT2 Day 1 S3 | 0 | 1 | 1 |
| WT2 Day 1 S4 | 0 | 2 | 1 |
| WT2 Day 1 S5 | 0 | 1 | 0 |
| WT2 5 Day S1 | 2.282 | 2 | 2 |
| WT2 5 Day S2 | 0 | 2 | 3 |
| WT2 5 Day S3 | 1.232 | 2 | 2 |
| WT2 5 Day S4 | 1.163 | 2 | 2 |
| WT2 5 Day S5 | 2.494 | 2 | 1 |
| WT3 Day 0 S1 | 0 | 0 | 0 |
| WT3 Day 0 S2 | 0 | 0 | 0 |
| WT3 Day 0 S3 | 0 | 0 | 0 |
| WT3 Day 0 S4 | 0 | 0 | 0 |
| WT3 Day 0 S5 | NWPOS | NWPOS | NWPOS |
| WT3 Day 0 S6 | NWPOS | NWPOS | NWPOS |
| WT3 Day 0 S7 | NWPOS | NWPOS | NWPOS |
| WT3 Day 0 S8 | 0 | 0 | 0 |
| WT3 Day 0 S9 | NWPOS | NWPOS | NWPOS |
| WT3 Day 0 S10 | 0 | 0 | 0 |
| WT3 Day 0 S11 | 0 | 0 | 0 |
| WT3 Day 0 S12 | 0 | 0 | 0 |
| WT3 Day 1 S1 | 0 | 1 | 0 |
| WT3 Day 1 S2 | 0 | 1 | 1 |
| WT3 Day 1 S3 | 1.779 | 1 | 1 |
| WT3 Day 1 S4 | 0.428 | 2 | 1 |
| WT3 Day 1 S5 | NWPOS | NWPOS | NWPOS |
| WT3 Day 1 S6 | 0.567 | 1 | 0 |
| WT3 Day 1 S7 | 0 | 1 | 1 |
| WT3 Day 1 S8 | 0 | 2 | 1 |
| WT3 Day 1 S9 | 0 | 1 | 0 |
| WT3 Day 1 S10 | 0 | 2 | 1 |
| WT3 Day 1 S11 | 0 | 2 | 0 |
| WT3 Day 1 S12 | 1.546 | 1 | 1 |
| WT3 Day 1 S13 | 0.000 | 1 | 0 |
| WT3 Day 1 S14 | 0.000 | 2 | 1 |
| WT3 Day 7 S1 | 4.091 | 3 | 4 |
| WT3 Day 7 S2 | 2.214 | 2 | 4 |
| WT3 Day 7 S3 | 2.709 | 3 | 4 |
| WT3 Day 7 S4 | 3.675 | 2 | 3 |
| WT3 Day 7 S5 | 2.51 | 3 | 3 |
| WT3 Day 7 S6 | 2.96 | 3 | 4 |
| WT3 Day 7 S7 | 2.797 | 2 | 4 |
| WT3 Day 7 S8 | 2.173 | 2 | 4 |
| WT3 Day 7 S9 | 1.673 | 2 | 2 |
| WT3 Day 7 S10 | 1.942 | 3 | 3 |
| WT3 Day 7 S11 | NWPOS | NWPOS | NWPOS |
| WT3 Day 7 S12 | 2.066 | 3 | 3 |
| WT3 Day 7 S13 | 4.082 | 3 | 2 |
| WT4 Day 0 S1 | 0 | 0 | 0 |
| WT4 Day 0 S2 | 0 | 0 | 0 |
| WT4 Day 0 S3 | 0 | 0 | 0 |
| WT4 Day 0 S4 | 0 | 0 | 0 |
| WT4 Day 0 S5 | 0 | 0 | 0 |
| WT4 Day 0 S6 | 0 | 0 | 0 |
| WT4 Day 1 S1 | 0.183 | 1 | 0 |
| WT4 Day 1 S2 | 0 | 1 | 0 |
| WT4 Day 1 S3 | 0 | 1 | 0 |
| WT4 Day 1 S4 | 0 | 1 | 0 |
| WT4 Day 1 S5 | 0 | 1 | 0 |
| WT4 Day 1 S6 | 0 | 1 | 0 |
| WT4 Day 1 S7 | 0 | 1 | 0 |
| WT4 Day 1 S8 | 0 | 2 | 0 |
| WT4 Day 1 S9 | 0 | 2 | 0 |
| WT4 Day 1 S10 | 0 | 2 | 0 |
| WT4 Day 5 S1 | 1.599 | 2 | 2 |
| WT4 Day 5 S2 | 2.627 | 3 | 3 |
| WT4 Day 5 S3 | 1.189 | 3 | 3 |
| WT4 Day 5 S4 | 1.507 | 3 | 2 |
| WT4 Day 5 S5 | 0 | 3 | 3 |
| WT4 Day 5 S6 | 0.486 | 2 | 3 |
| WT4 Day 5 S7 | 1.432 | 1 | 3 |
| WT4 Day 5 S8 | 1.080 | 1 | 3 |
| WT4 Day 5 S9 | 0.600 | 2 | 3 |
| WT4 Day 5 S10 | 1.326 | 1 | 3 |
| WT4 Day 7 S1 | 0.654 | 3 | 3 |
| WT4 Day 7 S2 | 0.691 | 3 | 3 |
| WT4 Day 7 S3 | 0.837 | 2 | 4 |
| WT4 Day 7 S4 | 0.885 | 2 | 2 |
| WT4 Day 7 S5 | 0.736 | 3 | 3 |
| WT4 Day 7 S6 | 2.383 | 3 | 3 |
| WT4 Day 7 S7 | 1.397 | 2 | 3 |

TABLE 3-continued

Re-epithelialization lengths, inflammation and granulation scores from histopathologic analysis of the sets of wounds 'WT2', 'WT3' and 'WT4'. The progressive increase in inflammation (score scale: 0 (lowest)-4 (highest)), re-epithelialization (in mm.) and granulation tissue scores (scale: 0 (lowest)-4 (highest)) in wounds at later time-points confirms the advancement of the wounds through different stages of healing. NWPOS: No wound present on slides. Some wound sections were desiccated or damaged and therefore could not be analyzed on the histopathologic slides.

| Sample | Re-epi (mm) | Inflammation | Granulation |
|---|---|---|---|
| WT4 Day 7 S8 | 0.603 | 2 | 3 |
| WT4 Day 7 S9 | 3.805 | 2 | 2 |
| WT4 Day 7 S10 | 0.000 | 3 | 3 |

TABLE 4

Test of significant difference (REGWQ test (ANOVA), confidence interval: 95%) between sets of factor loading values for wounds on different days (Y—Yes, N—No).

| | Significant Difference | | |
|---|---|---|---|
| Contrast | Factor 1 | Factor 2 | Factor 3 |
| Day 0 vs Day 1 | Y | Y | N |
| Day 0 vs Day 5 | Y | Y | Y |
| Day 0 vs Day 7 | Y | Y | Y |
| Day 1 vs Day 5 | Y | N | Y |
| Day 1 vs Day 7 | Y | Y | Y |
| Day 5 vs Day 7 | N | Y | N |

TABLE 5

Raman bands and qualitative intensities (w = weak, m = medium, s = strong) for each reference wound-bed constituent (very weak bands are not listed).

| Constituent | Raman bands (wavenumber, in $cm^{-1}$) |
|---|---|
| Collagen | 754 (w), 873 (w), 929 (w), 970 (w), 1003 (w), 1032 (w), 1064 (m), 1080 (m), 1297 (s), 1296 (s), 1440 (s), 1654 (s), 1746 (m), 2723 (m), 2851 (s), 2887 (s), 2932 (s), 3060 (w), 3326 (w) |
| Mouse Blood | 676 (m), 745 (s), 798 (w), 917 (w), 968 (m), 991 (s), 1088 (w), 1126 (s), 1167 (s), 1224 (s), 1305 (s), 1337 (s), 1367 (s), 1393 (s), 1431 (m), 1505 (w), 1560 (s), 1585 (s), 1636 (s), 2887 (s), 2926 (s), 2976 (m), 3066 (m), 3226 (m) |
| Elastin | 594 (w), 627 (w), 665 (w), 753 (w), 827 (w), 912 (m), 1007 (m), 1037 (w), 1133 (w), 1163 (w), 1256 (m), 1342 (m), 1420 (w), 1457 (m), 1527 (w), 1606 (m), 1670 (s), 2883 (s), 2940 (s), 2977 (s), 3062 (m) |
| Fibrin | 544 (w), 617 (w), 674 (w), 758 (w), 837 (w), 882 (w), 946 (w), 1002 (m), 1036 (w), 1235 (w), 1261 (w), 1292 (w), 1321 (w), 1406 (w), 1440 (m), 1550 (w), 1622 (m), 1644 (m), 1660 (m), 1704 (m), 2774 (w), 2870 (s), 2940 (s), 3060 (m), 2960 (s) |
| Fibronectin | 520 (w), 599 (w), 625 (w), 763 (s), 838 (m), 891 (m), 953 (m), 1004 (w), 1064 (s), 1136 (w), 1201 (w), 1251 (w), 1290 (w), 1413 (s), 1464 (s), 1609 (w), 2755 (w), 2894 (s), 2945 (s), 3286 (w), 3351 (w) |
| Hyaluronan | 895 (m), 948 (m), 1004 (w), 1048 (m), 1098 (s), 1126 (s), 1198 (w), 1251 (w), 1286 (w), 1331 (m), 1375 (s), 1406 (s), 1451 (m), 1645 (m), 2733 (w), 2900 (s), 2930 (s), 3331 (m) |
| Triolein | 594 (w), 770 (w), 817 (w), 843 (w), 971 (w), 1118 (w), 1264 (w), 1300 (m), 1440 (s), 1553 (w), 1653 (s), 1746 (m), 2327 (s), 2723 (w), 2851 (s), 2890 (s), 3004 (m) |

Analysis of Wounds in Live Animals

Figure 16:
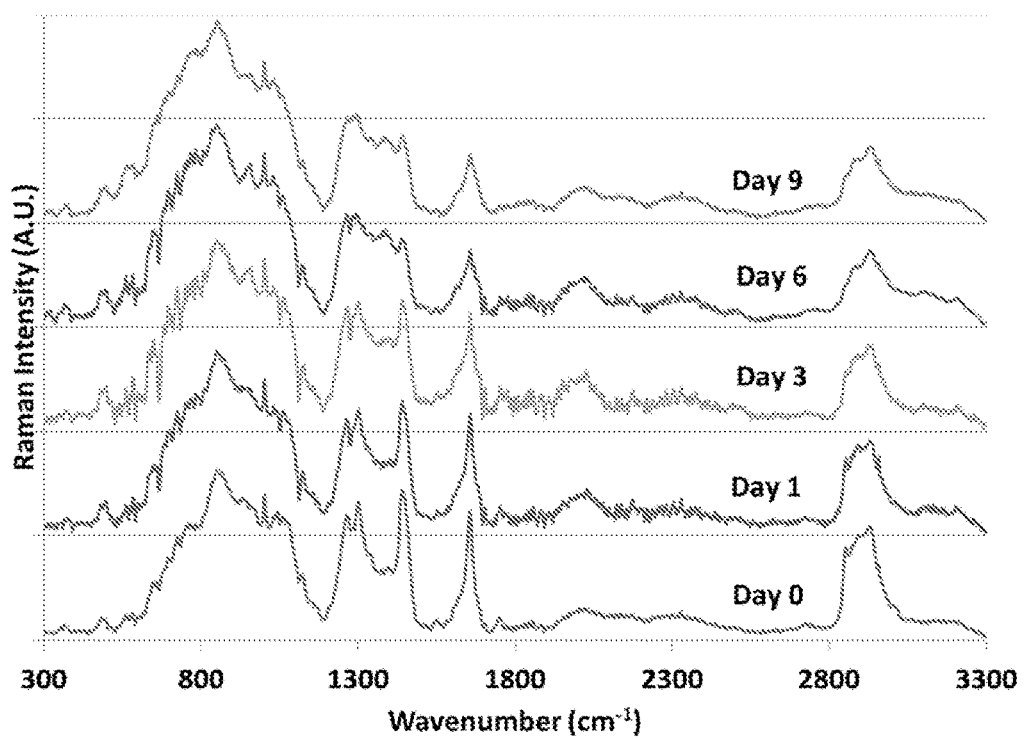
FIG. 16: Averaged Raman spectra obtained from live mice wounds using a fiber optic probe and 785 nm laser.

Experiments were also conducted where splinted wounds were made in mice (as reported previously) and Raman spectra (between wavenumbers 300-3300 $cm^{-1}$) were collected from live mice wounds (n=6) in vivo with the help of a fiber optic probe using laser operating at a wavelength of 785 nm as Raman excitation source. These experiments demonstrate that Raman spectra can be collected from live wounds in vivo using a fiber optic probe setup. We note that the 785 nm laser penetrates deeper into the wound tissue (~500 um) relative to 532 nm laser (~10-100 um) and the resultant Raman spectra reflects the averaged changes in the wound over a deeper volume. The averaged Raman spectra indicates differences in Raman intensity across the entire wavenumber change. Significant changes can be seen in the 2800-3000 $cm^{-1}$ and 1200-1700 $cm^{-1}$ region. See FIG. 16. The changes are broadly consistent with those seen before with a 532 nm laser as the Raman excitation source.

Figure 17:
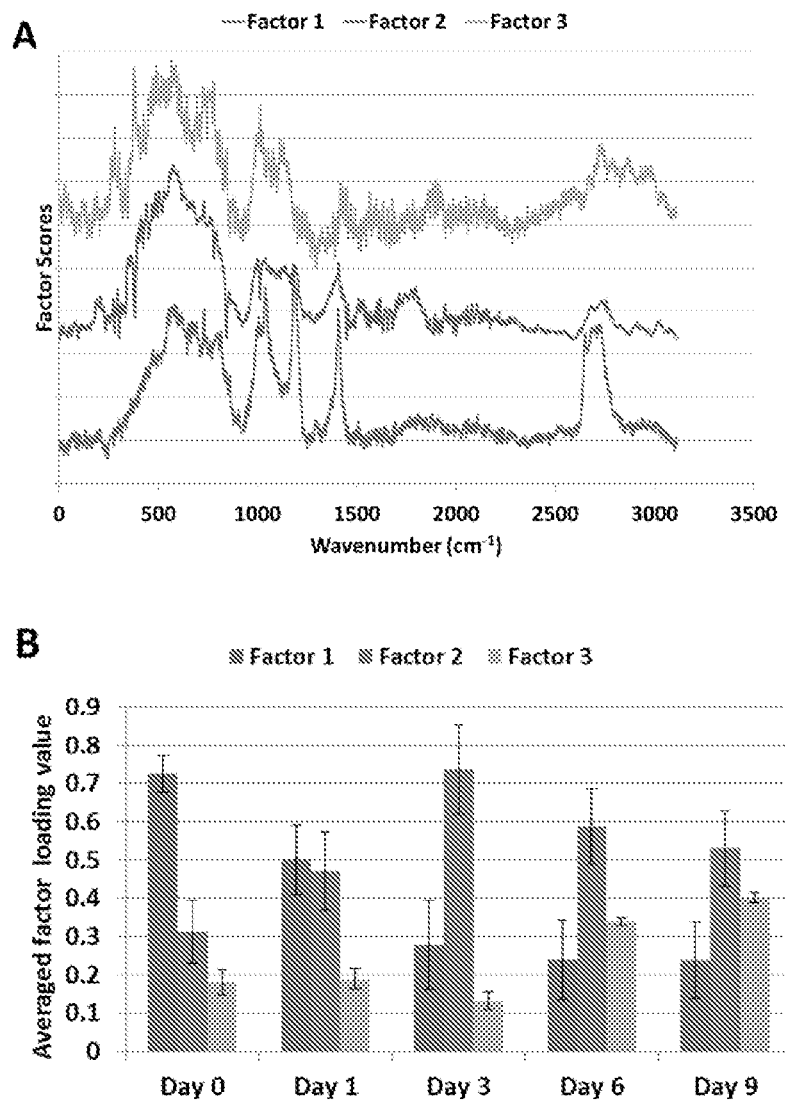
FIG. 17.
Figure 18:
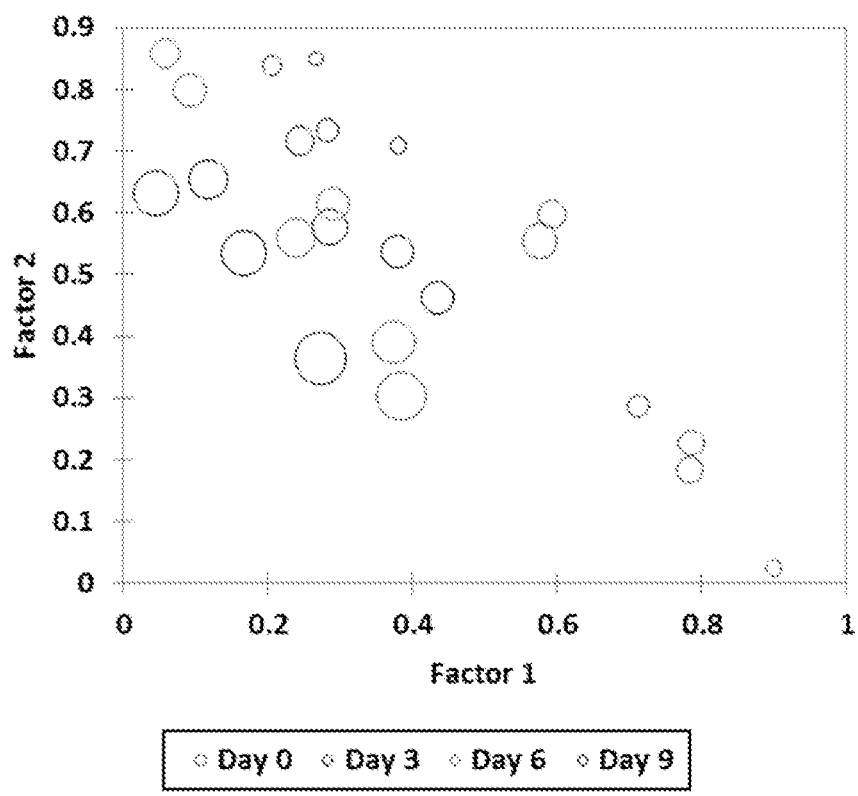
FIG. 18: A plot of factor loading values for all the wounds probed on different days. The axes represent factors 1 and 2 while the third factor is represented by the size of the circles. Wounds belonging to different days cluster around three sets of factor loadings (based on Raman spectroscopic characterization) which represent different stages of healing. The wounds represented in this graph were from a single experiment involving 6 wounds in 3 mice that were characterized at each time-point (Day 0/Day 3/Day 6/Day 9).

Multivariate factor analysis (MFA) was done on the spectral dataset as described above. The factor score spectra act as signatures for different stages of healing. See FIGS. 17 A and B. The factor loadingsfor wounds on different days show that the contribution of Factor 1 (representing hemostasis) decreases with time from 0.68±0.07 at day 0 to 0.23±0.1 at day 9 and that of 3 (representing proliferation) increases with time from 0.18±0.03 at day 0 to 0.4±0.01 at day 9. The factor loadings for Factor 2 (representing inflammation) first increase from 0.31±0.08 at day 0 to 0.73±0.1 at day 3 and then decreases to 0.53±0.09 at day 9. These results are consistent with those seen with the 532 laser and the microspectroscope setup employed before. FIG. 18 shows that the factor loading values of individual wounds at the same timepoint form clusters that can be distinguished from each other. The scatter in factor loading values in wounds at the same time-point are likely due to the different healing rates of different wounds in addition to the error due to spectral noise.

REFERENCES

1. Sen, C. K., et al. Human skin wounds: A major and snowballing threat to public health and the economy. *Wound Repair and Regeneration* 17, 763-771 (2009).

2. Sussman, C. & Bates-Jensen, B. M. *Wound care: a collaborative practice manual for physical therapists and nurses*, (Aspen Publishers, 1998).

3. Singer, A. J. & Clark, R. A. F. Mechanisms of disease—Cutaneous wound healing. *New England Journal of Medicine* 341, 738-746 (1999).

4. Hansen, G. L., Sparrow, E. M., Kokate, J. Y., Leland, K. J. & Iaizzo, P. A. Wound status evaluation using color image processing. *Medical Imaging, IEEE Transactions on* 16, 78-86 (1997).

5. Mostow, E. N. DIAGNOSIS AND CLASSIFICATION OF CHRONIC WOUNDS. *Clinics in Dermatology* 12, 3-9 (1994).
6. Goldman, R. J. & Salcido, R. More than one way to measure a wound: an overview of tools and techniques. *Advances in skin & wound care* 15, 236-243 (2002).
7. Bill, T. J., et al. Quantitative swab culture versus tissue biopsy: a comparison in chronic wounds. *Ostomy/wound management* 47, 34 (2001).
8. Alavi, A., Niakosari, F. & Sibbald, R. G. When and How to Perform a Biopsy on a Chronic Wound. *Advances in Skin & Wound Care* 23, 132-139 (2010).
9. Neidrauer, M. & Papazoglou, E. S. Optical Non-invasive Characterization of Chronic Wounds. *Bioengineering Research of Chronic Wounds: a Multidisciplinary Study Approach* 1, 381-404 (2009).
10. Miteva, M. & Romanelli, P. Histopathology of Wounds. *Measurements in Wound Healing*, 155-173 (2012).
11. Mark, M., et al. Histopathology in mouse metabolic investigations. *Current Protocols in Molecular Biology*, 29B. 24.21-29B. 24.32 (2007).
12. Morris, J. Information and observer disagreement in histopathology. *Histopathology* 25, 123-128 (1994).
13. Deolekar, M. & Morris, J. How accurate are subjective judgements of a continuum? *Histopathology* 42, 227-232 (2003).
14. Raman, C. V. & Krishnan, K. S. A new type of secondary radiation. *Nature* 121, 501-502 (1928).
15. Hanlon, E. B., et al. Prospects for in vivo Raman spectroscopy. *Physics in Medicine and Biology* 45, R1-R59 (2000).
16. Alimova, A., et al. In vivo molecular evaluation of guinea pig skin incisions healing after surgical suture and laser tissue welding using Raman spectroscopy. *Journal of Photochemistry and Photobiology B-Biology* 96, 178-183 (2009).
17. Crane, N. J., et al. Monitoring the healing of combat wounds using Raman spectroscopic mapping. *Wound Repair and Regeneration* 18, 409-416 (2010).
18. Flach, C. R., Zhang, G. J. & Mendelsohn, R. Raman Microscopy and Imaging: Applications to Skin Pharmacology and Wound Healing. in *Emerging Raman Applications and Techniques in Biomedical and Pharmaceutical Fields* (eds. Matousek, P. & Morris, M. D.) 365-384 (Springer, N.Y., 2010).
19. Schultz, G. S., et al. Wound bed preparation: a systematic approach to wound management. *Wound Repair and Regeneration* 11, S1-S28 (2003).
20. Edwards, R. & Harding, K. G. Bacteria and wound healing. *Current opinion in infectious diseases* 17, 91 (2004).
21. Percival, S. L. & Cutting, K. F. Biofilms: possible strategies for suppression in chronic wounds. *Nursing standard* (Royal College of Nursing (Great Britain): 1987) 23, 64, 66, 68 passim (2009).
22. Power, C., Wang, J., Sookhai, S., Street, J. & Redmond, H. Bacterial wall products induce downregulation of vascular endothelial growth factor receptors on endothelial cells via a CD14-dependent mechanism: implications for surgical wound healing. *Journal of Surgical Research* 101, 138-145 (2001).
23. C. Konturek, T. B., S J Konturek, S. Kwiecien, A. Dembinski, E G Hahn, P. Influence of bacterial lipopolysaccharide on healing of chronic experimental ulcer in rat. *Scandinavian journal of gastroenterology* 36, 1239-1247 (2001).
24. Wolcott, R. D., Rhoads, D. D. & Dowd, S. E. Biofilms and chronic wound inflammation. *Journal of wound care* 17, 333-341 (2008).
25. James, G. A., et al. Biofilms in chronic wounds. *Wound Repair and Regeneration* 16, 37-44 (2008).
26. Costerton, J., Stewart, P. S. & Greenberg, E. Bacterial biofilms: a common cause of persistent infections. *Science* 284, 1318-1322 (1999).
27. Bjarnsholt, T., et al. Why chronic wounds will not heal: a novel hypothesis. *Wound repair and regeneration* 16, 2-10 (2008).
28. Rhoads, D., Wolcott, R. & Percival, S. Biofilms in wounds: management strategies. *Journal of wound care* 17, 502-508 (2008).
29. Hannig, C., Folio, M., Hellwig, E. & Al-Ahmad, A. Visualization of adherent microorganisms using different techniques. *Journal of Medical Microbiology* 59, 1-7 (2010).
30. Daims, H. & Wagner, M. In situ techniques and digital image analysis methods for quantifying spatial localization patterns of nitrifiers and other microorganisms in biofilm and flocs. *Methods in Enzymology, Vol 46: Research on Nitrification and Related Processes, Pt B* 496, 185-215 (2011).
31. Miller, C. N., et al. Assessing bacterial burden in wounds: comparing clinical observation and wound swabs. *International Wound Journal* 8, 45-55 (2011).
32. Phillips, P., et al. Bacterial biofilms in wounds. *Wound Healing Southern Africa* 1, 10-12 (2009).
33. Galiano, R. D., Michaels, J., Dobryansky, M., Levine, J. P. & Gurtner, G. C. Quantitative and reproducible murine model of excisional wound healing. *Wound Repair and Regeneration* 12, 485-492 (2004).
34. Wojdyr, M. Fityk: a general-purpose peak fitting program. *Journal of Applied Crystallography* 43, 1126-1128 (2010).
35. Rummel, R. J. *Applied factor analysis*, (Northwestern University Press, 1970).
36. Malinowski, E. R. Factor analysis in chemistry. Wiley, N.Y. (1991).
37. Hendrickson, A. E. & White, P. O. Promax—a quick method for rotation to oblique simple structure. *British Journal of Statistical Psychology* 17, 65-70 (1964).
38. Abdi, H. Factor rotations in factor analyses. *Encyclopedia for Research Methods for the Social Sciences. Sage: Thousand Oaks, Calif.*, 792-795 (2003).
39. Pelton, J. T. & McLean, L. R. Spectroscopic methods for analysis of protein secondary structure. *Analytical Biochemistry* 277, 167-176 (2000).
40. Dehring, K. A., Smukler, A. R., Roessler, B. J. & Morris, M. D. Correlating changes in collagen secondary structure with aging and defective type II collagen by Raman spectroscopy. *Applied Spectroscopy* 60, 366-372 (2006).
41. De Gelder, J., De Gussem, K., Vandenabeele, P. & Moens, L. Reference database of Raman spectra of biological molecules. *Journal of Raman Spectroscopy* 38, 1133-1147 (2007).
42. Tu, A. T. Peptide backbone conformation and microenvironment of protein side chains. *Advances in infrared and Raman spectroscopy* 13, 47-112 (1986).
43. Gniadecka, M., Nielsen, O. F., Christensen, D. H. & Wulf, H. C. Structure of water, proteins, and lipids in intact human skin, hair, and nail. *Journal of Investigative Dermatology* 110, 393-398 (1998).
44. Gniadecka, M., et al. Water and protein structure in photoaged and chronically aged skin. *Journal of Investigative Dermatology* 111, 1129-1133 (1998).

45. Tunc, S., et al. In situ conformational analysis of fibrinogen adsorbed on Si surfaces. *Colloids and Surfaces B-Biointerfaces* 42, 219-225 (2005).
46. Schwinte, P., et al. Stabilizing effects of various polyelectrolyte multilayer films on the structure of adsorbed/embedded fibrinogen molecules: An ATR-FTIR study. *Journal of Physical Chemistry B* 105, 11906-11916 (2001).
47. Chen, Y. L., et al. Conformational changes of fibrinogen adsorption onto hydroxyapatite and titanium oxide nanoparticles. *Journal of Colloid and Interface Science* 214, 38-45 (1999).
48. Bramanti, E., Benedetti, E., Sagripanti, A. & Papineschi, F. Determination of secondary structure of normal fibrin from human peripheral blood. *Biopolymers* 41, 545-553 (1997).
49. Grinnell, F. FIBRONECTIN AND WOUND-HEALING. *Journal of Cellular Biochemistry* 26, 107-116 (1984).
50. Clark, R. A. F., et al. FIBRONECTIN AND FIBRIN PROVIDE A PROVISIONAL MATRIX FOR EPIDERMAL-CELL MIGRATION DURING WOUND REEPITHELIALIZATION. *Journal of Investigative Dermatology* 79, 264-269 (1982).
51. Osterlund, E., Eronen, I., Osterlund, K. & Vuento, M. SECONDARY STRUCTURE OF HUMAN-PLASMA FIBRONECTIN—CONFORMATIONAL CHANGE INDUCED BY CALF ALVEOLAR HEPARAN SULFATES. *Biochemistry* 24, 2661-2667 (1985).
52. Shafer-Peltier, K. E., et al. Raman microspectroscopic model of human breast tissue: implications for breast cancer diagnosis in vivo. *Journal of Raman Spectroscopy* 33, 552-563 (2002).
53. Midwood, K. S., Williams, L. V. & Schwarzbauer, J. E. Tissue repair and the dynamics of the extracellular matrix. *International Journal of Biochemistry & Cell Biology* 36, 1031-1037(2004).
54. Aberg, K. M., et al. Psychological stress downregulates epidermal antimicrobial peptide expression and increases severity of cutaneous infections in mice. *Journal of Clinical Investigation* 117, 3339-3349 (2007).
55. Kitagawa, T. & Hirota, S. Raman spectroscopy of proteins. *Handbook of vibrational spectroscopy* (2002).
56. Edwards, H. Spectra-Structure Correlations in Raman Spectroscopy. in *Handbook of Vibrational Spectroscopy*, Vol. 3 (eds. Chalmers, J. & Griffiths, P.) 1838-1871 (John Wiley and Sons, 2002).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

The invention claimed is:

1. A method of characterizing a wound comprising:
collecting a plurality of Raman spectra from a wound in a patient, wherein said collecting comprises analyzing a wound in a live subject with a fiber optic probe operably linked to a Raman microspectroscope, and
via a processor, comparing said plurality of Raman spectra with one or more basis spectra to determine one or more factor loadings, and
correlating said factor loadings to the healing stage of the wound.

2. The method of claim 1, wherein said Raman microspectroscope is a handheld Raman microspectroscope.

3. The method of claim 1, wherein said wound is illuminated with a laser emitted from said fiber optic probe at a desired wavelength.

4. The method of claim 1, wherein said healing stage is selected from the group consisting of hemostasis, the inflammation stage and the proliferative stage.

5. The method of claim 1, further comprising the step of determining a course of treatment based on the healing stage identified by comparison of the one or more Raman spectra with one or more basis spectra.

6. The method of claim 1, further comprising identifying healing and non-healing portions in the same wound on basis of their Raman spectra to inform a course of treatment selective to the non-healing portions.

7. The method of claim 1, further comprising the step of using said Raman spectra to identify the presence of microorganisms.

8. The method of claim 7, wherein said microorganisms are associated in a biofilm.

9. The method of claim 1, wherein said plurality of Raman spectra are decomposed by multivariate factor analysis to provide one or more factor loading values corresponding to said healing stage of a wound.

10. The method of claim 9, wherein said plurality of Raman spectra are decomposed by multivariate factor analysis to provide three factor loading values each corresponding to a respective wound healing stage.

11. The method of claim 10, wherein said wound healing stage is selected from the group consisting of the hemostasis stage, the inflammation stage and the proliferative stage.

12. A system for analysis of wound healing comprising a Raman microspectroscope in operable association with a computer processor, said computer processor comprising a nontransitory computer readable medium comprising a database of basis spectra derived from Raman spectroscopic analysis of a plurality of wound beds and computer executable code that compares Raman spectra collected from a subject via said Raman microspectroscope with said basis spectra to determine a stage of wound healing.

13. The system of claim 12, wherein said Raman microspectroscope is handheld.

14. The system of claim 13, wherein said basis spectra correspond to stages of wound healing.

* * * * *